(12) United States Patent
Chu

(10) Patent No.: US 8,790,240 B2
(45) Date of Patent: Jul. 29, 2014

(54) SYSTEMS AND METHODS EMPLOYING A PUSH TUBE FOR DELIVERING A URETHRAL SLING

(75) Inventor: Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/430,204

(22) Filed: Mar. 26, 2012

(65) Prior Publication Data

US 2012/0245411 A1 Sep. 27, 2012

Related U.S. Application Data

(63) Continuation of application No. 11/122,712, filed on May 5, 2005, now Pat. No. 8,142,345.

(60) Provisional application No. 60/508,600, filed on Oct. 3, 2003, provisional application No. 60/569,300, filed on May 6, 2004.

(51) Int. Cl.
*A61F 2/02* (2006.01)

(52) U.S. Cl.
USPC .......................................................... 600/30

(58) Field of Classification Search
USPC ......... 600/29–32, 37; 606/119, 151; 128/834, 128/885
See application file for complete search history.

(56) References Cited

U.S. PATENT DOCUMENTS

| | | | |
|---|---|---|---|
| 5,337,736 A | 8/1994 | Reddy | |
| 6,241,736 B1 | 6/2001 | Sater et al. | |
| 6,382,214 B1 | 5/2002 | Raz et al. | |
| 6,423,080 B1 | 7/2002 | Gellman et al. | |
| 6,494,887 B1 | 12/2002 | Kaladelfos | |
| 6,502,578 B2 | 1/2003 | Raz et al. | |
| 6,612,977 B2 | 9/2003 | Staskin et al. | |
| 6,638,209 B2 | 10/2003 | Landarebe | |
| 6,641,525 B2 | 11/2003 | Rocheleau et al. | |
| 6,652,450 B2 | 11/2003 | Neisz et al. | |
| 6,660,010 B2 | 12/2003 | Gellman | |
| 6,802,807 B2 | 10/2004 | Anderson et al. | |
| 6,911,003 B2 | 6/2005 | Anderson et al. | |
| 2002/0147382 A1 | 10/2002 | Neisz et al. | |
| 2002/0151910 A1 | 10/2002 | Gettman et al. | |
| 2002/0161382 A1 | 10/2002 | Neisz et al. | |

(Continued)

OTHER PUBLICATIONS

Petros, et al, "Urethral Pressure Increase on Effort Originates From Within The Urethrea, and Continence From Musculovaginal Closure," Neurology and Urodynamics, 14(4):337-350 (1995).

(Continued)

*Primary Examiner* — Christine Matthews

(57) ABSTRACT

In a general aspect, a method of treating urinary incontinence can include slidably interfitting a first push tube into a first dilator tube disposed at an end of a sling assembly and slidably interfitting the first push tube onto an end of a shaft of a delivery device. The method can also include inserting the shaft transvaginally through a vaginal wall and removing the shaft to implant a portion of the sling assembly in periurethral tissue. The method can also include slidably interfitting a second push tube into a second dilator tube disposed at a second end of the sling assembly and slidably interfitting the second push tube onto the end of the shaft. The method can still further include inserting the shaft transvaginally through the vaginal wall and removing the shaft from the patient to implant a second portion of the sling assembly in periurethral tissue.

18 Claims, 15 Drawing Sheets

(56) References Cited

U.S. PATENT DOCUMENTS

| | | |
|---|---|---|
| 2003/0050530 A1 | 3/2003 | Neisz et al. |
| 2003/0171644 A1 | 9/2003 | Anderson et al. |
| 2003/0176875 A1 | 9/2003 | Anderson et al. |
| 2004/0015048 A1 | 1/2004 | Neisz et al. |
| 2004/0087970 A1 | 5/2004 | Chu et al. |

OTHER PUBLICATIONS

Petros, "Ambulatory Sugery for Urinary Incontinence and Vaginal Prolapse," Medical Journal of Australia, 161:171-172 (1994).

Petros et al., "An Integral Theory and its Method for the Diagnosis and Management of Female Urinary Incontinence," Scandinavian J. Urology and Nephrology, Supplement 153:1-93 (1993).

Petros, "An Integral Theory of Bladder Neck Opening, Closure and Urinary Incontinence in the Female," International Journal of Gynecology & Obstetrics, XXIII World Congress of Gynecology and Obstetrics (Figo) (1991).

Petros, "The Intravaginal Slingpasty Operation, A Minimally Invasive Technique for Cure of Urinary Incontinence in the Female," Aust. Nz J. Obstet Gynaecol., 36(4):453-461 (1996).

Ulmsten et al, "Intravaginal Slingpasty (IVS): An Ambulatory Surgical Procedure for Treatment of Female Urinary Incontinence," Scand J. Urology Nephrol 29(1):75-82 (1995).

Ulmsten et al, "A Multicenter Study of Tension-Free Vaginal Tape (TVT) for Surgical Treatment of Stress Urinary Incontinence," Int Urogynecol J., 9(4):210-213 (1998).

Ulmsten et al, A Three-Year Follow Up of Tension Free Vaginal Tape for Surgical Treatment of Female Stress Urinary Incontinence, British J. of Obstetrics and Gyn., 106:345-350 (1999).

Ulmsten et al, "An Ambulatory Surgical Procedure Under Local Anesthesia for Treatment of Female Urinary Incontinence," The International Urogynecology Journal, 7:81-86 (1996).

Ulmsten et al, "An Introduction to Tension-Free Vaginal Tape (TVT)—A New Surgical Procedure for Treatment of Female Urinary Incontinence," Int. Urogynecol J. (Suppl. 2):S3-4 (2001).

Ulmsten et al, "Connective Tissue Factors in the Aeticology of Female Pelvic Disorders," Ann. Med. 22(6):3 (1990).

Ulmsten et al, "Intravaginal Slingplasty," Zentravil Bynakol., 116:398-404 (1994).

Ulmsten et al., "Surgery for Female Urinary Incontinence," Current Opinion in Obstetrics & Gynecology, 4(3):456-462 (1992).

Ulmsten, "The Basic Understanding and Clinical Results of Tension-Free Vaginal Tape for Stress Urinary Incontinence," Der Urologe, [A] 40:269-273 (2001).

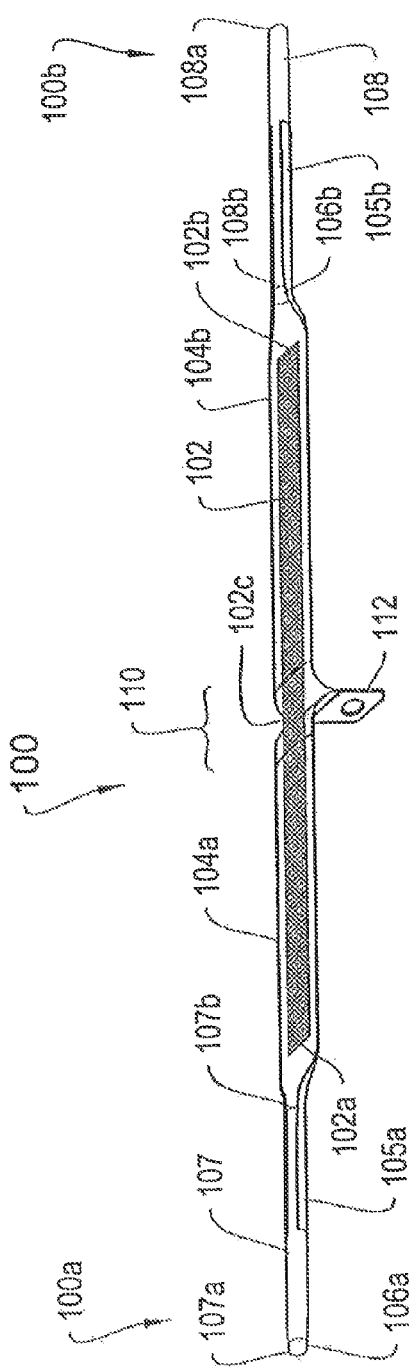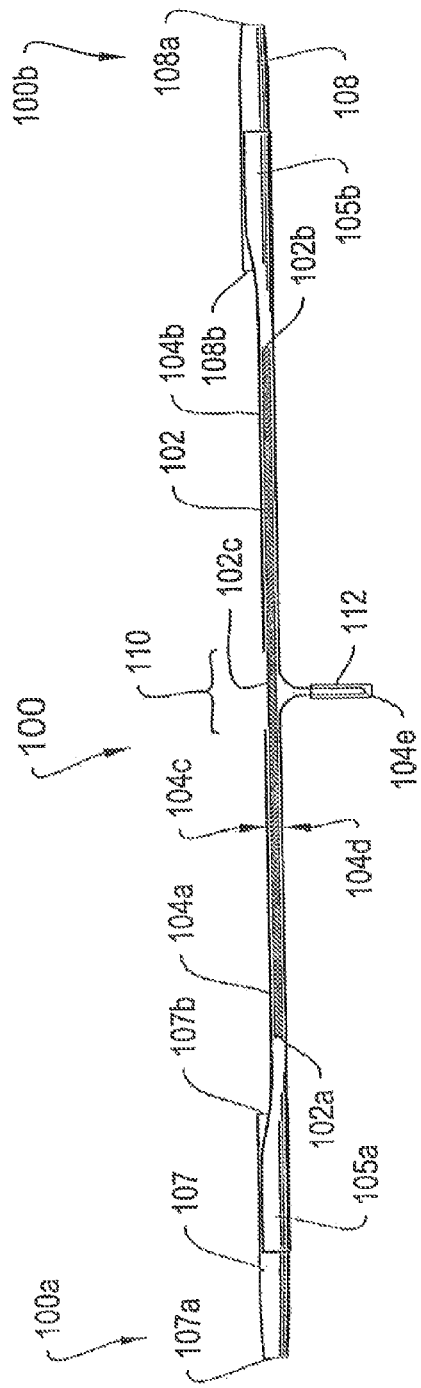
Figure 1A
Figure 1B

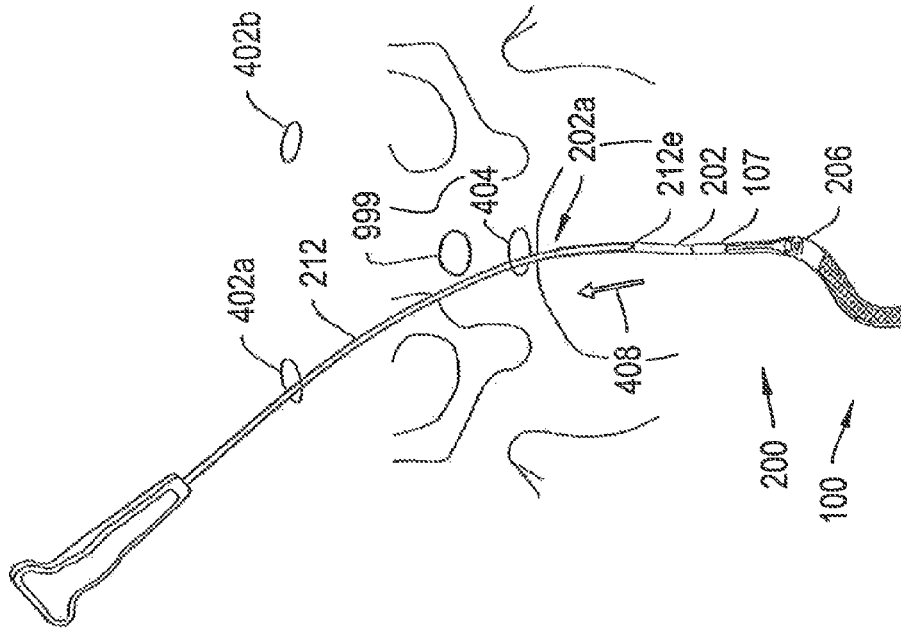
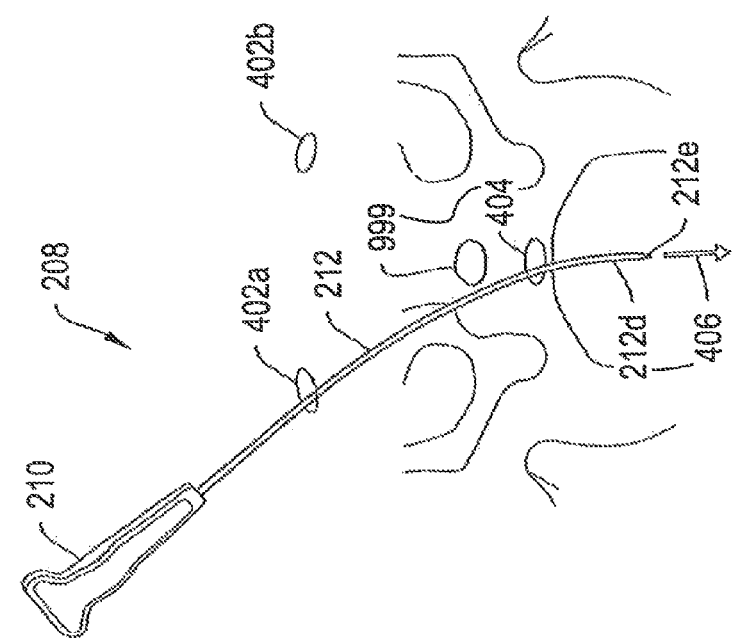

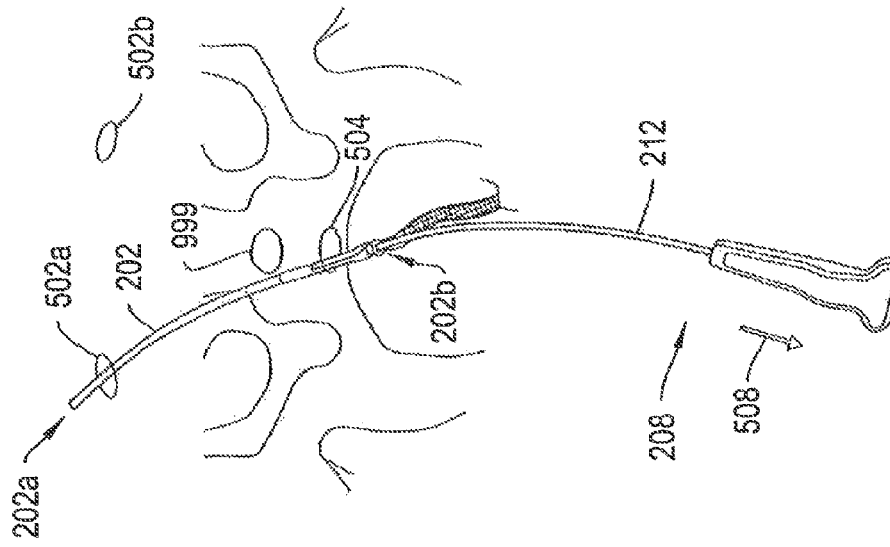
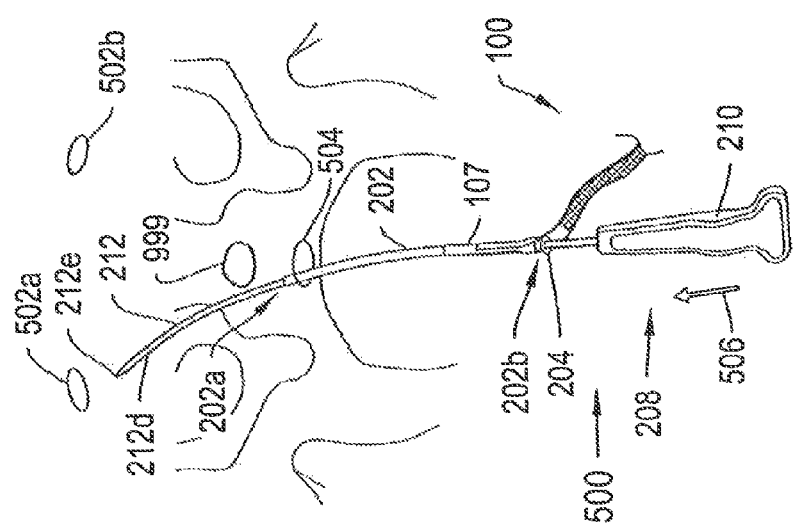

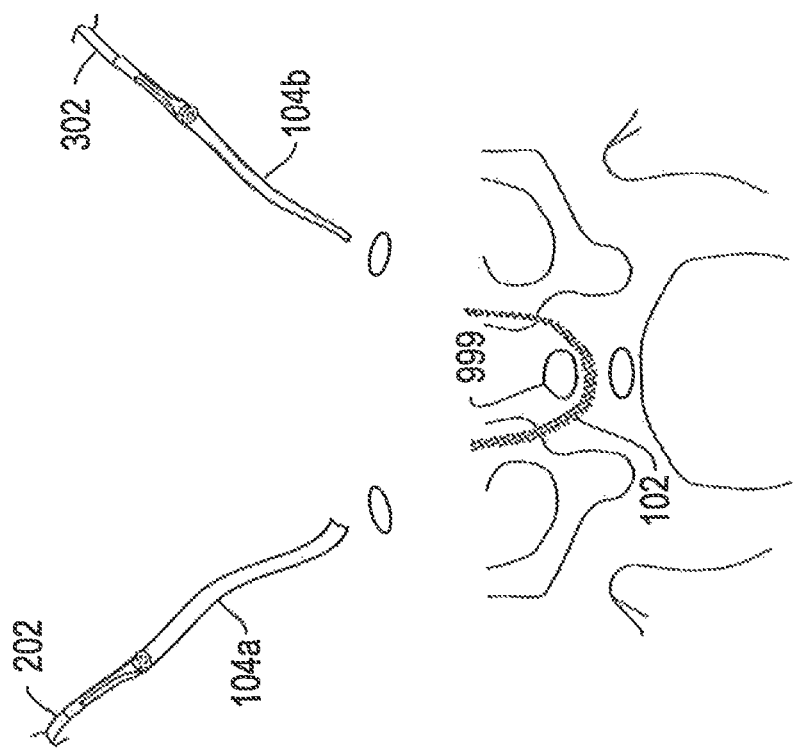

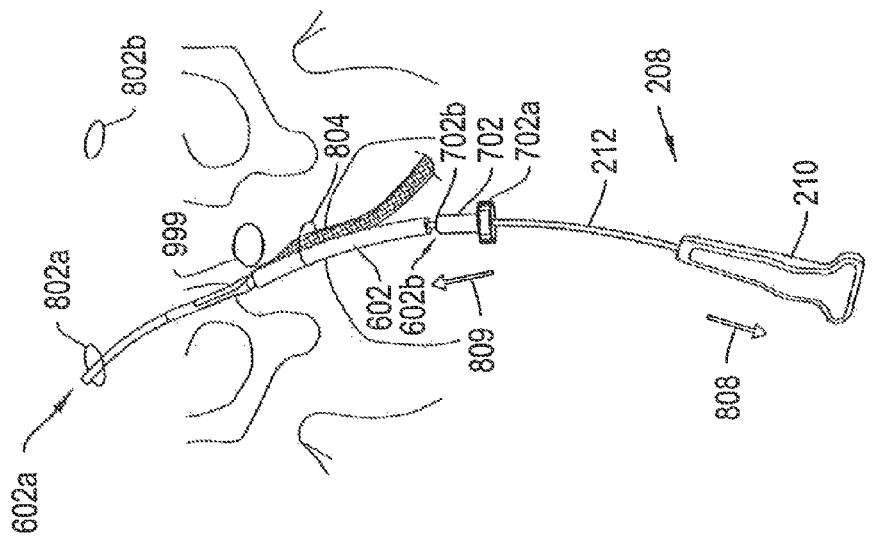
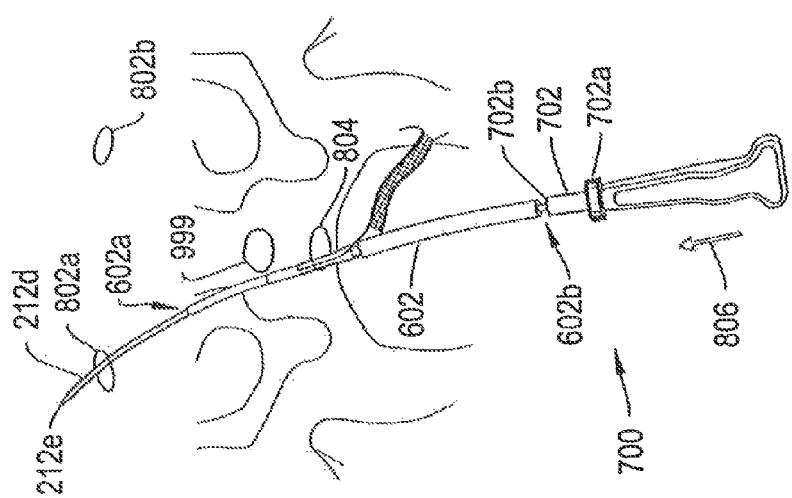
Figure 8B
Figure 8A

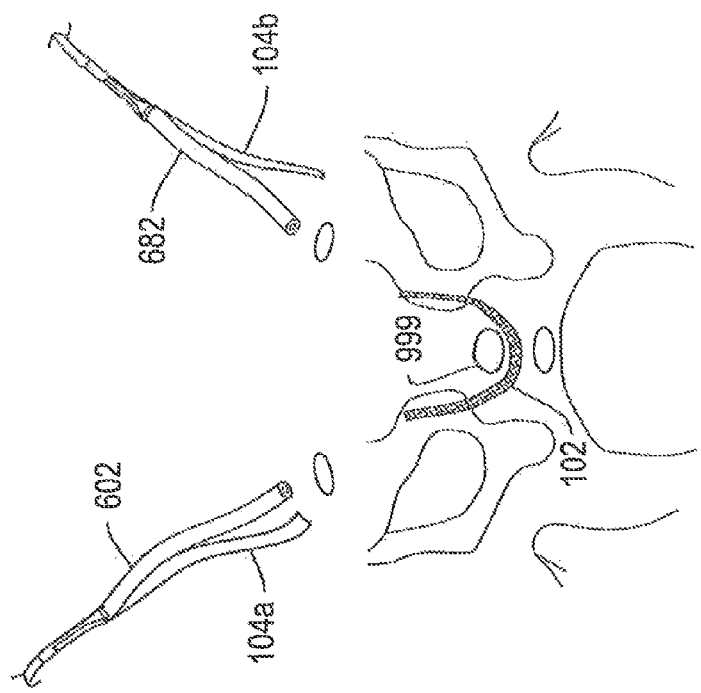
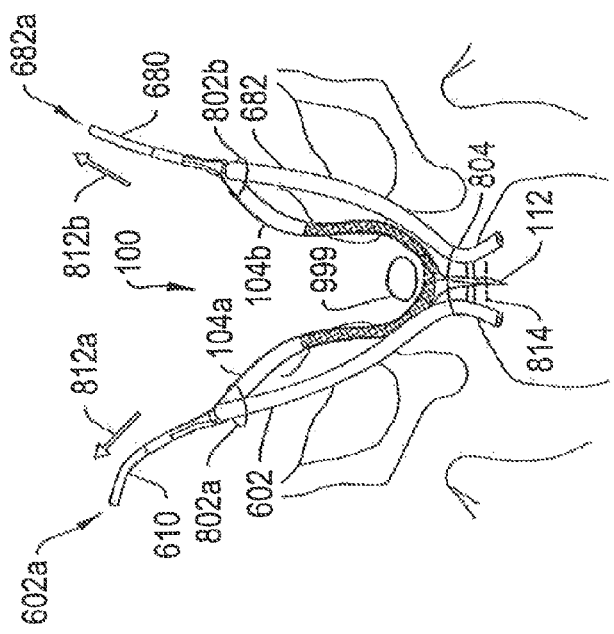
Figure 8D
Figure 8C

SYSTEMS AND METHODS EMPLOYING A PUSH TUBE FOR DELIVERING A URETHRAL SLING

CROSS REFERENCE TO RELATED APPLICATIONS

This application is a continuation of prior patent application Ser. No. 11/122,712, filed May 5, 2005, which claims the benefit of and priority to U.S. Provisional Patent Application Ser. No. 60/508,600 filed on Oct. 3, 2003, and U.S. Provisional Patent Application Ser. No. 60/569,300 filed on May 6, 2004, which are hereby incorporated by reference in their entirety.

FIELD OF THE INVENTION

The invention generally relates to systems and methods for delivering an implantable sling to an anatomical location in a patient. In various embodiments, the invention is directed to systems and methods relating to the use of a push tube during sling delivery.

BACKGROUND OF THE INVENTION

Anatomical tissues may become weakened or damaged by age, injury, or disease. This decrease in the structural integrity of anatomical tissues may have significant medical consequences. Even in the absence of tissue necrosis, weakening of an anatomical structure may impair one or more of the biological functions of the tissue. To help alleviate this impact on biological function, implantable, supportive slings have been developed. These slings can be implanted into a patient to provide support for the weakened or damaged tissue. The support provided by the sling mimics the natural position and structure of the tissue, and thereby helps decrease or eliminate impairment of biological function resulting from tissue weakening or damage. Although supportive slings have been used in numerous contexts to address the weakening of a variety of anatomical tissues, they have proven particularly useful for decreasing urinary incontinence resulting from weakening or damage to urethral, periurethral and/or bladder tissue.

Stress urinary incontinence (SUI) affects primarily women, but also men, and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvis floor is distended, weakened, or damaged, causing the bladder neck and proximal urethra to rotate and descend in response to increases in intra-abdominal pressure (e.g., due to sneezing, coughing, straining, etc.). As a result, the patient's response time becomes insufficient to promote urethral closure and, consequently, the patient suffers from urine leakage and/or flow. SUI has a variety of causes including, but not limited to, pregnancy, aging, infection, injury, congenital defect, and disease.

A popular treatment of SUI involves placement of implantable slings under the bladder neck or the mid-urethra to provide a urethral platform. Placement of the sling limits the endopelvis fascia drop. There are various methods for placing the sling. Slings can be affixed and stabilized using traditional bone anchoring approaches, as well as recently developed anchor-less approaches. Additionally, a variety of implantation procedures, including various routes of administration, exist. These procedures provide physicians with a range of implantation options. Physicians can readily select amongst the various implantation procedures based on numerous patient-specific factors including, but not limited to, age, gender, overall health, location of tissue defect, the degree of tissue impairment, and the like. Furthermore, physicians can select from amongst numerous sling delivery devices that facilitate sling placement.

Despite the numerous advances in sling design, implantation methodologies, and delivery devices, no single method and/or device is appropriate for every situation. Accordingly, devices, systems, and methods that offer new approaches for sling implantation would be advantageous to the medical community.

SUMMARY OF THE INVENTION

The invention addresses deficiencies of the prior art by providing devices, systems and methods for facilitating delivery of an implant to an anatomical site. According to a preferred embodiment, the device can be used to deliver an implant, such as a sling for treating urinary incontinence, to a mid-urethral location of a patient. The methods and systems of the invention simplify the delivery of the implant by using a delivery system including a push tube.

In one aspect, the invention provides a sling delivery system comprising a sling assembly including an implantable sling, sized and shaped for providing a urethral platform. The sling assembly may also include a sleeve for covering, at least partially, the sling. In preferred embodiments, the sling is free floating inside the sleeve and does not attach to the sleeve or anything else. The sleeve may have a gap exposing a portion of the sling. The sleeve includes a looped portion, covered at least partially by a tab, extending out of the plane of the sleeve and the sling. In some embodiments, the tab prevents the sleeve from being removed from the sling, and cutting the tab permits sleeve removal. The sling assembly also includes first and second dilator tubes, possessing longitudinally extending through lumens and located at first and second ends of the sling assembly. In some embodiments, the dilator tubes attach to ends of the sleeve. In other embodiments, the dilator tubes also or alternatively attach to ends of the sling.

In preferred embodiments, the sling delivery system includes one or more push tubes for slidably interfitting within the dilator tubes of the sling assembly. The push tube includes a shoulder or flared end where the external diameter of the push tube is substantially greater than the remaining portion of the push tube. The shoulder is sized and shaped to prevent its passage through the lumen of the dilator tube and may be located at an end or intermediate location of the push tube. In some embodiments, the shoulder may abut an end of the dilator tube. The push tube may have a uniform or variable diameter and may include a tapered tip. The push tube also includes a longitudinally extending through lumen, which runs the length of the push tube.

According to some aspects, the sling delivery system includes a delivery device including a shaft attached to a handle. The shaft of the delivery device is sized and shaped to slidably fit within the lumen of the push tube. Similarly, the lumen of the push tube is sized and shaped for slidably interfitting over the shaft of the delivery device. According to one feature, this configuration enables the push tube to rotate freely about the shaft and enables the dilator tube to rotate freely about the push tube. Such rotation reduces twisting or other deformation of the sling and sling/sleeve combination during sling placement. The shaft of the delivery device may be inserted into the lumen of the push tube from either end of the push tube. The shaft and the handle of the delivery device may be substantially in the same plane or in different planes, and the shaft may include sections located in different panes. One or more parts or the shaft may assume a curved, angled, halo, helical, or any other suitable shape including substantially straight. The shaft includes a distal tip that may be conical in shape and may have a sharp or blunt end. The tip may be designed for percutaneous punctuation and/or advancement through tissue of a patient.

According to a feature of the invention, the delivery device of the sling delivery system includes an optional pusher mechanism, which slidably interfits onto the shaft of the delivery device such that the pusher mechanism can freely slide over any portion of the shaft. The pusher mechanism includes a grasping area for grasping by a medical operator and a distal surface for abutting an end of the push tube. A medical operator can advance the pusher mechanism distally along the shaft of the delivery device to facilitate sliding of the push tube off the shaft.

In some embodiments, the push tube includes a window section where a portion of the push tube wall is removed, absent, or cat out, thus exposing the lumen. The window section, which is intermediate to the ends of the push tube, facilitates sliding of the shaft within the lumen of the push tube.

in another embodiment of the invention, the push tube includes two end portions, located near ends of the push tube, and an intermediate portion, which is smaller in outer diameter than the end portions and is located at an intermediate position between the end portions. The intermediate portion is sized and shaped to slidably move through the lumen of the dilator tube. Shoulders, formed by the transitions between the end portions and the intermediate portion, can abut an interior end and an exterior end of the dilator tube, trapping the dilator tube between the shoulders of the push tube.

According to one aspect, the invention provides a method for treating urinary incontinence comprising implanting a surgical sling into the body of a patient via a vaginal cavity, comprising the steps of inserting a shaft of a delivery device transabdominally through the vaginal wall of a patient, slidably interfitting a push tube onto an end of the shaft extending through the vaginal wall, and removing the shaft from the patient to implant a portion of the sling in the periurethral tissue in the body of the patient. In some embodiments, the method includes the step of sliding the push tube along the shaft until it extends through an abdominal incision prior to removing the shaft. The method may also include the step of grasping the push tube where it extends through the abdominal incision prior to removing the shaft. According to a further embodiment, the steps of the method may be repeated with a second push tube.

According to another aspect, the invention provides a method for treating urinary incontinence comprising implanting a surgical sling, into the body of a patient via a vaginal cavity, comprising the steps of slidably interfitting a push tube onto an end of a shaft of a delivery device, inserting the shaft transvaginally through the vaginal wall of a patient, and removing the shaft from the patient to implant a portion of the sling in the periurethral tissue in the body of the patient. In some embodiments, the method includes the step of sliding the push tube along the shaft until it extends through an abdominal incision prior to removing the shaft. The method may also include the step of grasping the push tube where it extends through the abdominal incision prior to removing the shaft. In some embodiments, the step of sliding the push tube is actuated by a pusher mechanism. According to a further embodiment, the steps of the method may be repeated with a second push tube.

According to a feature of the invention, the sling delivery systems and devices of the invention may be sized and shaped for abdominal, transvaginal, or transobtural procedures. Additionally, the methods of the invention may include positioning at least one of a first end and a second end of a sling and/or sling assembly in front of the pubic bone, behind the pubic bone, near the pubic bone, and/or near or through an obturator foramen.

Other aspects and advantages of the invention are described below.

BRIEF DESCRIPTION OF THE DRAWINGS

The following figures depict illustrative embodiments of the invention in which like reference numerals refer to like elements. These depicted embodiments may not be drawn to scale and are to be understood as illustrative of the invention and not as limiting in any way.

FIGS. 1A-1B depict perspective and side views, respectively, of a sling assembly according to an illustrative embodiment of the invention.

FIGS. 4A-F depict a method for introducing a sling via a transabdominal implantation method according to an illustrative embodiment of the invention.

FIG. 5A-E depict a method for introducing a sling via a transvaginal implantation method according to an illustrative embodiment of the invention.

FIGS. 8A-D depict a method for introducing a sling via a transvaginal implantation method according to an illustrative embodiment of the invention.

ILLUSTRATIVE DESCRIPTION

Figure 2:
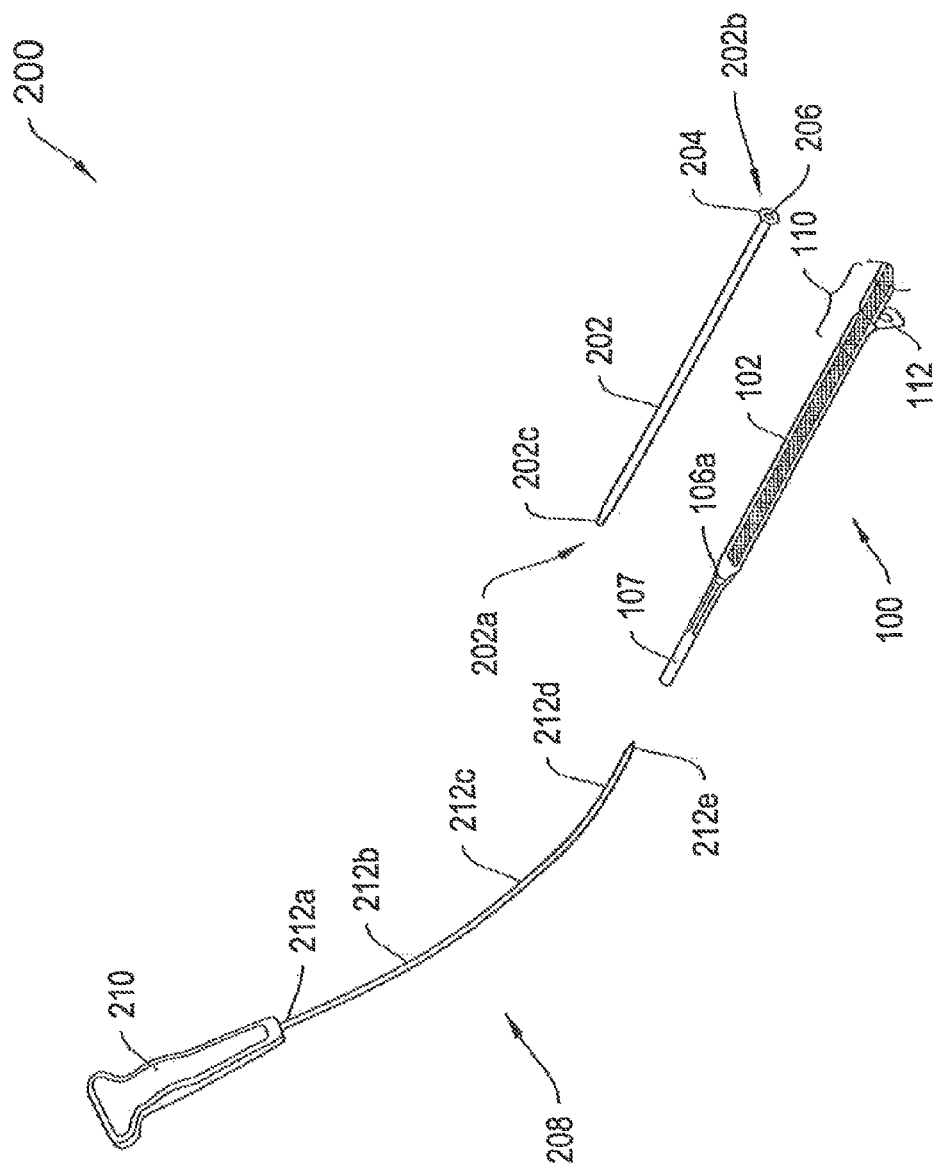
FIG. 2 depicts a sling delivery system employing the sling assembly of FIG. 1.

As described above in summary, the invention in various illustrative embodiments is directed to systems, devices, and methods employing a push tube to deliver a sling to the periurethral tissues of a patient.

FIG. 1A shows a front perspective view of a sling assembly 100 of the type employed with a push tube of the invention. As shown, the sling assembly 100 has first 100a and second 100b ends. The sling assembly 100 includes a sling 102 and a sleeve 104 for covering, at least partially, the sling 102. The sling 102 is free floating inside the sleeve 104. The sleeve 104 has first 104a and second 104b portions. The sleeve 104 also includes first and second end portions 105a and 105b, respectively. The sling assembly 100 also includes first 107 and second 108 dilator tubes. The tubes 107 and 108 have exterior ends 107a and 108a, respectively, as well as interior ends 107b and 108b, respectively. The tubes 107 and 108 also have longitudinally extending through lumens 106a and 106b, respectively. The sling 102 and the sleeve 104 are further described below.

FIG. 1B shows a side view of the sling assembly 100. The sleeve portion 105a wraps partially around and attaches to the dilator tube 107. Attachment may be by any suitable mechanism, including, without limitation, heat bonding, gluing, stapling, stitching, shrink wrapping or the like. The sleeve portion 105b attaches to the dilator tube 108 in a similar fashion. In other illustrative embodiments, the sling end portions 102a and 102b may attach to the dilator tubes 107 and 108, respectively, in a similar fashion. Alternatively, the dilator tubes 107 and 108 may be directly attached to the ends of the sling 102a and 102b.

The longitudinally extending through lumens 106a and 106b run the length of dilator tubes 107 and 108, respectively. In some embodiments, the lumens 106a and 106b have a uniform diameter. In other embodiments, the lumens 106a and 106b have one or more locations of increased and/or decreased diameter. For example, the dilator tube walls, which define the lumens 106a and 106h, may have bumps, ridges, shoulders, grooves, or other internal protuberances, which may increase or decrease the size of the lumens 106a and 106b.

As shown in FIG. 1B, an opening or gap 110 is located near a midpoint of a top surface 104c of the sleeve 104. The gap 110 exposes a portion 102c of the sling 102 where the entire width of the sling 102 is exposed. In other embodiments, the sleeve 104 covers the sling 102 completely. Additionally, in some embodiments, there may more than one gap along the length of the sleeve 104 where the sling 102 is not covered by the sleeve 104.

According to the illustrative embodiment, the sleeve portions 104a and 104b are formed as an integral sleeve 104 having a continuous bottom side 104d. The bottom side 104d includes a looped portion 104e. The looped portion 104e of the sleeve 104 extends downward out of the plane of the sleeve portions 104a and 104b and the sling 102, for example, at an angle of about 90 degrees. The looped portion 104e is covered by a tab 112, which fits over the looped portion 104e. In other embodiments, the sleeve portions 104a and 104b may be separate sections fastened to each other on the bottom side 104d by way of a fastener or the tab 112.

Although the looped portion 104e and the gap 110 are shown at the mid-point of the sleeve 104, in other illustrative embodiments, the looped portion 104e and the gap 110 may be near the mid-point of sleeve 104, but not at the mid-point, or even substantially off set from the mid point.

The tab 112 can be used during implantation as a visual aid for placement of the sling 102. According to the illustrative embodiment, the tab 112 also inhibits, or in some embodiments, prohibits the sleeve 104 from sliding off, or otherwise being removed from, the sling 102 during sling assembly placement. Preferably, the tab 112 must be cut to enable the sleeve 104 to slide off the sling 102. According to one embodiment, cutting the tab 112 enables the sleeve portions 104a and 104b to be slid off the sling ends 102a and 102b, respectively. This feature ensures that the sleeve 104 cannot be removed simply by applying a pulling force, for example, on the sleeve end sections 105a and 105b or on the tab 112. Such a force may be applied to the sling assembly ends by a medical operator during sling assembly placement.

During placement, after the sling assembly 100 is positioned within the patient, a cut is made through the center of the tab 112, and thus through the looped portion 104e of the sleeve 104, allowing the two sleeve portions 104a and 104b to be separated from each other. The sleeve portions 104a and 104b are then slid off of the sling 102, out of the body of the patient by pulling on the two sleeve portions 104a and 104b, the sleeve end portions 105a and 105b, the two dilator tubes 107 and 108, or generally on the two ends 100a and 100b of the sling assembly 100. A more detailed description of the tab 112 and other mechanisms of fastening the sleeve portions 104a and 104b are provided in the co-pending U.S. patent application Ser. No. 10/642,395 entitled "Systems, Methods and Devices Relating to Delivery of Medical Implants," the entire disclosure of which is incorporated by reference herein.

The sleeve 104 may be made, for example, from one or more absorbent materials, such as a sponge-like material, which can optionally be pre-soaked in a drug solution, for example, in an anesthetic, anti-inflammatory, coagulating, anticoagulating, and/or antibiotic solution. In other embodiments, the sleeve 104 may be made from a non-wettable material, such as polypropylene, polyethylene, polyester, polytetrafluoroethylene (available from DuPont Corporation, Wilmington, Del., under the trademark TEFLON®), TYVEK®, MYLAR®, or co-polymers thereof. The non-wettable materials can also be pretreated with a therapeutically effective drug treatment. The sleeve 104 is preferably transparent so that an operator can to see the sling 102 inside the sleeve 104. In some embodiments, the sling 102 and/or sleeve 104 may be colored to facilitate placement of the sling by the operator. The sleeve 104 may include both transparent and colored sections.

According to the illustrative embodiment, the sling 102 is from about 1 to 3 cm in width and from about 10 to 45 cm in length, and terminates at free ends. The sling 102 is shown to be rectangular, but it may have another suitable shape. The sling 102 may have a uniform thickness over its entire length and/or width. Alternatively, the thickness can be suitably varied at one or more locations. According to the illustrative embodiment, the thickness of the sling 102 material ranges from about 0.02 to about 0.10 cm.

According to the illustrative embodiment, the length of the sling 102 is shorter than the length of the sleeve 104, and the sling 102, including both ends 102a and 102b, does not connect to the sleeve 104 or anything else. During sling assembly placement, this feature enables a medical operator to pull on the sling assembly ends 100a and 100b, for example, via the dilator tubes 107 and 108, and/or any of the delivery devices to be used for placement, without risk of stretching, curling or otherwise deforming the sling 102.

In the illustrative embodiment, the sling 102 is made entirely of polypropylene. However, sling 102 may be fabricated from any of a number of biocompatible materials, such as nylon, polyethylene, polyester, polypropylene, fluoropolymers, copolymers thereof, combinations thereof, or other suitable synthetic material(s). The material may be, for example, a synthetic material that is absorbable by the patient's body, such as polyglycolic acid, polylactic acid, and other suitable absorbable synthetic materials. Alternatively, the material for the sling 102 may be derived from mammalian tissue(s) or a combination of mammalian tissue(s) and synthetic material(s). The sling material may be fabricated from one or more yarns, which yarns may be made from one or more materials. The sling 102 may incorporate or be coated with one or more agents to provide a therapeutic effect, for example, to reduce discomfort, to reduce the chance of infection and/or to promote tissue growth.

As mentioned above, in one exemplary embodiment, the length of the slim 102 is shorter than the length of the sleeve 104, and the sling 102 does not connect to the sleeve 104 or anything else. This feature inhibits the medical operator from gripping the free ends of the sling 102 and inadvertently tensioning the sling 102. This feature may be further enhanced by making the sling 102 long enough to support the urethra, but not long enough to expose the ends 102a and 102b of the sling outside the body. This has the advantage of preventing infection caused by the exposure of the sling 102 external to the body. By way of example, an illustrative sleeve 104 may be about 1 cm, 2 cm, 3 cm, 4 cm, 5 cm, 6 cm, 7 cm, 8 cm, 9 cm, or 10 cm longer than the sling 102. According to other illustrative embodiments, the sleeve 104 may be about 10 cm, 15 cm, 20 cm, 25 cm, or 30 cm longer than the sling 102. In particular, in transobtural procedures, the sling 102 may be configured to be long enough to extend to, or through, both obturator foramen, but not long enough to extend outside of the body. In other embodiments, the sling 102 may be configured in length to extend outside of the body, when placed, and the ends then trimmed to length by the physician to a point just under the skin.

In one illustrative embodiment, the edge regions of the sling 102 can be configured differently depending on their intended placement in the body of the patient. For example, a midsection of the sling is typically located where an anatomical site, such as a mid-urethral or bladder neck location in the periurethral tissue, needs to be supported. In one illustrative embodiment, the midsection of the sling 102 has smooth or rounded edges, hereinafter also referred to as "non-tanged" or "de-tanged." According to a further illustrative embodiment, other sections of the sling may include tangs (e.g., sharp projections or frayed edges). The tangs are generally useful for anchoring the sling 102 and/or encouraging tissue growth into the sling. Anchoring the sling 102 in this manner generally obviates the need for additional sutures to hold the sling in place.

The tanged and non-tanged edges of the sling 102 can be formed in a plurality of ways. For example, the sling 102 can be cut from a woven sheet, in which case the edges would be initially tanged along the entire length of the sling. One or more non-tanged sections may be formed by any process that smoothes, rounds or removes the sharp edges of the tangs. For example, the tangs may be heat-smoothed by burning or melting the tangs. In one embodiment, the non-tanged section has a length of about 1 to about 5 cm, preferably about 2 to about 2.5 cm, on either or both sides of the center line of the sling. Providing one or more non-tanged sections, which may be in close proximity to a sensitive anatomical site in the patient, can enhance the comfort level of the patient and reduce the potential for the edges of the tangs to erode or irritate the urethra. Alternatively, the sling 102 can be produced from a woven tape having the approximate finished width of the sling. The smooth sides of the tape can then be trimmed of to produce the tanged sections.

Without limitation, any suitable sling assembly 100 may be employed with the invention. Examples of slings, sling assemblies, delivery devices and implantation approaches with features that may be employed in the present invention are disclosed in U.S. Pat. No. 6,666,817, entitled "Expandable Surgical. Implants and Methods of Using Them," U.S. Pat. No. 6,669,706, entitled "Thin Soft Tissue Surgical Support Mesh," U.S. Pat. No. 6,375,662, entitled "Thin Soft Tissue Surgical Support Mesh," U.S. Pat. No. 6,042,592, entitled "Thin Soft Tissue Surgical Support Mesh," U.S. patent application Ser. No. 10/015,114, entitled "Devices for Minimally Invasive Pelvic Surgery," U.S. patent application Ser. No. 10/774,826, entitled "Devices for Minimally Invasive Pelvic Surgery," U.S. patent application Ser. No. 10/093,398, entitled "System for Implanting an Implant and Method Thereof," U.S. patent application Ser. No. 10/093,498, entitled "System for Implanting an Implant and Method Thereof," U.S. patent application Ser. No. 10/093,371, entitled "System for Implanting an Implant and Method Thereof," U.S. patent application Ser. No. 10/093,424, entitled "System for Implanting an Implant and Method Thereof," U.S. patent application Ser. No. 10/093,450, entitled "System for Implanting an Implant and Method Thereof," U.S. patent application Ser. No. 10/094,352, entitled "System for Implanting an Implant and Method Thereof," U.S. patent application Ser. No. 10/631,364, entitled "Bioabsorbable Casing for Surgical Sling Assembly," U.S. patent application Ser. No. 10/641,376, entitled "Spacer for Sling Delivery System," U.S. patent application Ser. No. 10/641,487, entitled "Systems, Methods and Devices Relating to Delivery of Medical Implants," U.S. patent application Ser. No. 10/642,395, entitled "Systems, Methods and Devices Relating to Delivery of Medical Implants," U.S. patent application Ser. No. 10/642,397, entitled "Systems, Methods and Devices Relating to Delivery of Medical Implants," U.S. patent application Ser. No. 10/832,653, entitled "Systems and Methods for Sling Delivery and Placement," U.S. patent application Ser. No. 10/939,191, entitled "Devices for Minimally Invasive Pelvic Surgery," U.S. Provisional Patent Application Ser. No. 60/508,600, filed on Oct. 3, 2003 and U.S. Provisional Patent Application Ser. No. 60/569,300, filed on May 6, 2004, and U.S. patent application Ser. No. 10/957,926, entitled "Systems and Methods for Delivering a Medical Implant to an Anatomical Location in a Patient," filed on Oct. 4, 2004, the entire contents of all of which are incorporated herein by reference.

FIG. 2 shows a perspective view of sling delivery system 200. The system 200 includes a sling assembly 100, a push tube 202, and a delivery device 208. The push tube 202 contains a first end 202a and a second end 202b. The push tube 202 includes a shoulder or flared end 204 located at second end 202b where the external diameter of the push tube is substantially greater than the remaining portion of the push tube. The push tube 202 also includes a longitudinally extending through lumen 206, which runs the length of the push tube between the first 202a and the second 202b ends. The delivery device 208 includes a handle 210 and a shaft 212.

The push tube 202 is sized and shaped to slidably interfit within the lumen 106a the dilator tube 107. The push tube 202 may have a uniform diameter or it may gradually increase or decrease in outside diameter one or more times to provide, for example, bumps, ridges, and/or grooves, etc. The push tube 202 may be made from materials similar to those used to make the sling 102 or the sleeve 104. For example, the push tube 202 may be made from any of a number of biocompatible materials, such as nylon, polyethylene, polyester, polypropylene, fluoropolymers, copolymers thereof, combinations thereof, or other suitable synthetic material(s). The push tube 202 may incorporate or be coated with one or more agents to provide a therapeutic effect, for example, to reduce discomfort, to reduce the chance of infection and/or to promote tissue growth.

The shoulder 204 is sized and shaped to prevent passage of the shoulder 204 through the lumen 106a of the dilator tube 107, i.e. the shoulder 204 extends radially beyond the diameter of the lumen 106a. The push tube 202 also includes a longitudinally extending through lumen 206. In some embodiments, the lumen 206 has a uniform diameter. In other embodiments, the lumen 206 has one or more locations of increased and/or decreased diameter. For example, the push tube walls, which define the lumen 206, may have bumps, ridges, shoulders, grooves, or internal protuberances, which may increase or decrease the size of the lumen 206. The push tube 202 also includes a tip 202c, which is tapered and/or of decreased outer diameter relative to the rest of the push tube 202. For example, the tip 202c may be conical in shape.

The shaft 212 may be, for example, any suitable needle, cannula, tubular member, tunneler, dilator or the like. In the illustrative embodiment, the shaft 212 is attached to the handle 210 at a proximal end 212a and contains a first substantially straight portion 212b. The proximal end 212a permanently affixes to the handle 210, and the first straight portion 212b extends distally from the first end 212a to a curved portion 212c. The curved portion 212c extends distally from the first end 212a to a second substantially straight portion 212d. The second straight portion 212d extends distally from the first end 212a and terminates at a distal tip 212e. The distal tip 212e may be conical in shape and may have a sharp or blunt end. A blunt end provides some resistance to unintended penetration through tissue or organ, such as the bladder. The tip 212e may be designed for percutaneous punctuation and/or advancement through tissue of a patient.

The shaft 212 of the delivery device 208 is sized and shaped to fit within the lumen 206 of the push tube 202. Similarly, the lumen 206 of the push tube 202 is sized and shaped for slidably interfitting over the shaft 212 of the delivery device 208. According to one feature, this configuration enables the push tube 202 to rotate freely about the shaft 212 and enables the dilator tube 107 to rotate freely about the push tube 202. Such rotation reduces twisting or other deformation of the sling and sling/sleeve combination during sling placement. The cross-section of the shaft 212 may have a constant shape and size, or its shape and size may vary along the length of the shaft 212. The cross-section of the shaft 212 may assume any shape, for example, circular, semi-circular, oval, triangular or rectangular. In other embodiments, one or more sections of the shaft 212, for example the first straight section 212b may include an enlarged, flared portion to dilate tissue beyond the typical diameter of the shaft 212. The shaft 212 may have a tapered diameter, which may aid in dilation and tunneling through tissue and in entering into lumen 206. The shaft 212 may also have one or more coatings, for example, to facilitate insertion of the shaft into a body of a patient or into the lumen 206.

In one illustrative embodiment, the shaft 212 is formed from a rigid material, for example, a metal or a polymeric material. Examples of suitable metals include, but are not limited to, stainless steel, titanium, and alloys such as nitinol. Suitable polymers, which can be used as a coating on a metal to form the shaft 212, include but are not limited to, plastics such as polytetrafluoroethylene (PTFE). In some embodiments, the shaft has some flexibility, and can be described as semi-rigid. The shaft 212 may be solid or hollow. If the shaft 212 is at least partly hollow, it may include a lumen (not shown) with one or more openings along the shaft 212, for example, at the distal tip 212e or along the side of the shaft 212.

Although in the illustrative embodiment of FIG. 2 the shaft 212 and the handle 210 are substantially in the same plane, in other embodiments, at least one section of the shaft and the handle are located in different planes. Similarly, the shaft 212 may include sections located in different planes. One or more parts or the shaft 212 may assume a curved, angled, halo, helical, or any other suitable shape including substantially straight.

According to the illustrative embodiment, the surface of the shaft 212 is substantially smooth. However, in other illustrative embodiments, the shaft 212 may include texturing, such as stippling, to provide increased traction relative to a gloved hand of a medical operator. In other embodiments, the surface of the shaft 212 may be coated with one or more drugs such as anesthetic, anti-inflammatory, coagulating, anticoagulating, antibiotic or antimicrobial agents. The drug may be delivered to the patient's tissue while the shaft 212 is in contact with the tissue. The surface of the shaft may be coated with a light-absorbing coating to reduce glare, for example, under a cystoscope. The coating may be a polymer, such as PTFE, or other suitable material, such as a plastic film, and may be colored to aid in detection. The coating may aid in introduction of the shaft 212 into the body of a patient or aid in interfitting of the shaft 212 with the lumen 206 of the push tube 202. The surface of the shaft 212 may be painted so that one can easily tell it apart from surrounding tissue and fluid under a cystoscope to make it easier to detect under the cystoscope.

Figure 3:
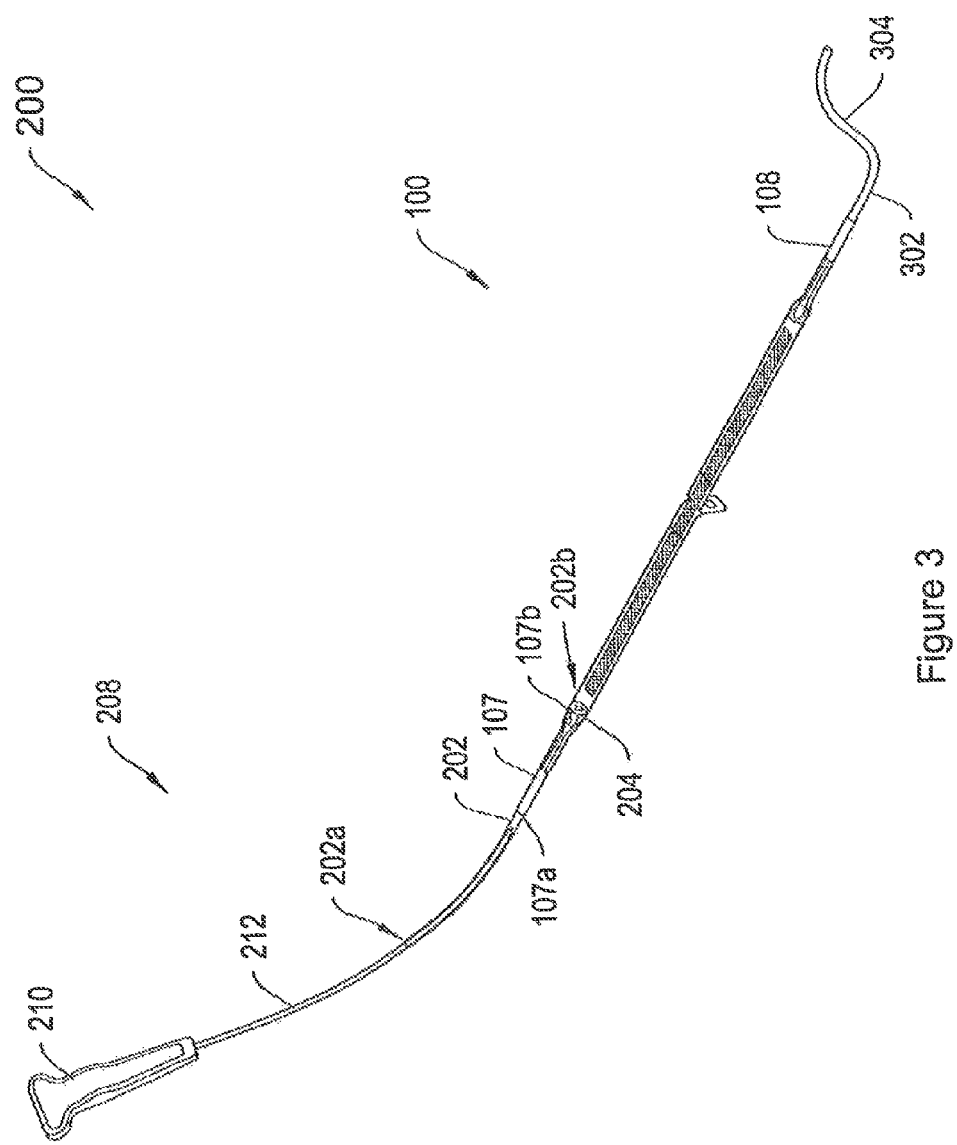
FIG. 3 depicts the sling delivery system of FIG. 2 assembled for implanting a sling via a transabdominal implant method.

FIG. 3 shows a perspective view of the sling delivery system 200 assembled as shown. The push tube 202 is interfits within the lumen 106a of the dilator tube 107 of the sling assembly 100 such that the first end 202a of the push tube 202 extends beyond the exterior end 107a of dilator tube 107 and the second end 202b of the push tube 202 extends beyond the interior end 107b of the dilator tube.

The push tube 202 is sized and shaped to slidably move through the lumen 106a of the dilator tube 107. In the illustrative embodiment, the push tube 202 is free to advance through the dilator tube 107 in the direction of the exterior end 107a of the dilator tube 107 until the flared shoulder 204 of the push tube 202 abuts the interior end 107h of the dilator tube 107. The diameter of the shoulder 204 is greater than the diameter of the lumen 106a of the dilator tube 107, and prevents the push tube 202 from advancing completely through the dilator tube 107 in the direction of the exterior end 107a.

The shaft 212 of delivery device 208 slidably interfits into the first end 202a of the lumen 206 of the push tube 202. In other embodiments, the shaft 212 may be inserted into the second end 202b of the push tube 202. In some embodiments, the push tube 202 is flexible and can bend and conform to the shape of the dilator tube 107 and/or the shape of the shaft 212 of the delivery device 208. In other embodiments, the push tube 202 is semi-rigid or rigid. Although in FIG. 3 the shaft 212 is depicted as being curved for a transabdominal or a transvaginal implantation procedure, the shaft 212 may be shaped in any suitable manner and include substantially straight, angled, halo (e.g., a curved section existing in substantially a single plane different than the plane of the handle), and/or helical (e.g., a curved section spiraling through multiple planes) portions. Other shaft shapes, such as a halo and/or helical shape, may be suitable for other implantation methods, such as a transobtural method.

FIG. 3 also depicts a second push tube 302 having all the features of the push tube 202. As shown, the push tube 302 slidably interfits with a dilator tube 108. The push tube 302 may also have one or more curved or kinked sections 304, illustrating that the push tubes 302 and 202 may be flexible. While the push tube 302 is not shown to be associated with a delivery device, another delivery device analogous to the delivery device 208 may be provided for interoperating with the push tube 302. Alternatively, the single delivery device 208 may be employed with both push tubes 202 and 302 separately.

Figure 4D:
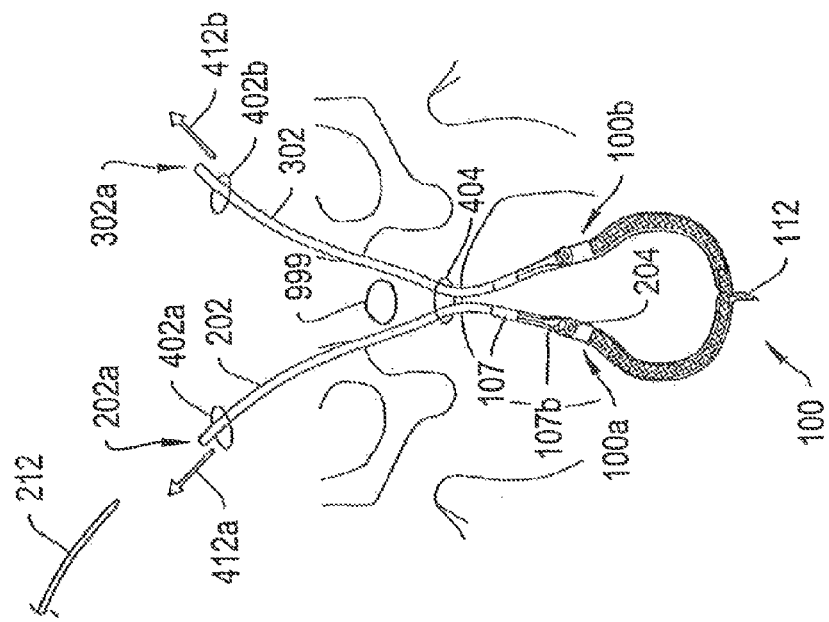

FIGS. 4A-F conceptually depict an illustrative method for introducing a sling 102 via a transabdominal implantation approach using the sling delivery system 200 shown in FIGS. 2 and 3. As shown in FIG. 4A, incisions 402a and 402b are made on each side of the midline of the body in the lower abdomen along with an incision 404 made in the vaginal wall of the patient. The shaft 212 of delivery device 208 is inserted into the abdominal incision 402a to create a passage down along the posterior surface of the pubic bone through body tissue. The passage is created by moving the shaft 212 in from the abdominal incision 402a and out through the vaginal incision 404 in the direction of the arrow 406. The shaft 212 is inserted until the tip 212e and at least some of the straight portion 212d extend from the vaginal incision 404 out of the body.

A shown in FIG. 4B, the first end 202a of the push tube 202 of the assembled sling delivery system 200 of FIG. 3 is then slid over the shaft tip 212e in the direction of the arrow 408 and advanced up the shaft 212 into the body. The push tube 202 may be advanced partially into the body or completely such that the first end 202a emerges from the body at the abdominal incision 402a.

Figure 4C:
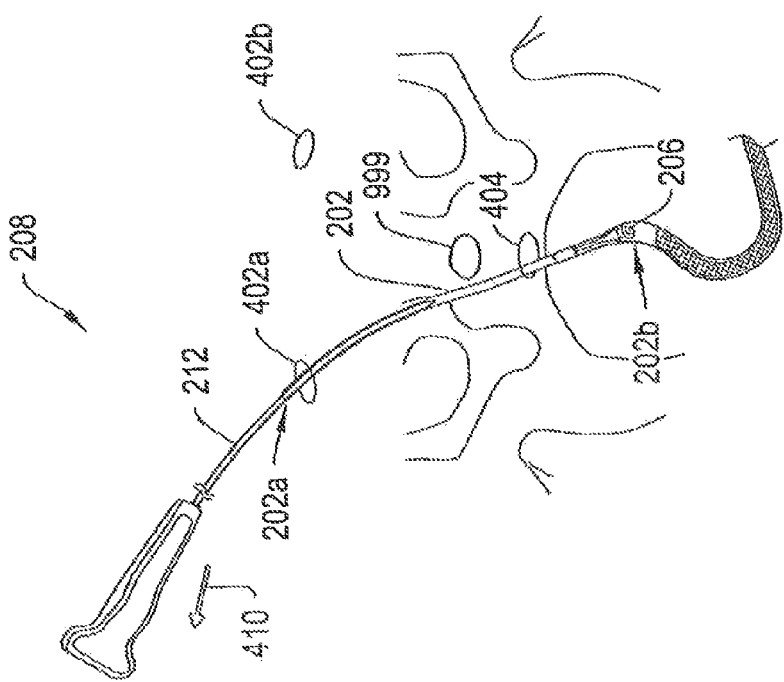

As shown FIG. 4C, the shaft 212 is then withdrawn from the body of the patient out the abdominal incision 402a in the direction of the arrow 410. According to a further feature, withdrawal of the shaft 212 pulls the push tube 202 by way of frictional force further into the body of the patient and partially out of the incision 402a. Once the first end 202a protrudes out from incision the 402a, it is then grasped by the medical operator and held while the delivery device 208 is pulled in the direction of the arrow 410 to remove the shaft 212 from the lumen 206 of the push tube 202, leaving the push tube 202 within the body of the patient.

As shown in FIG. 4D, the procedures described above for FIGS. 4A-C are then repeated with the delivery device 208 and the push tube 302 on the contralateral side of the body. With both push tubes 202 and 302 inserted, a cystoscopy may be performed to verify correct placement and ensure bladder integrity. Subsequent to placement verification, the medical operator grasps the push tube ends 202a and 302a and gently pulls in the direction of the arrows 412a and 412b, respectively. This pulls the push tubes 202 and 302 through the body from the vaginal incision 404 at least partially out the abdominal incisions 402a and 402b, respectively. By pulling alternatively on the ends 202a and 302a, the operator places the sling assembly 100 at the desired location under the urethra 999. During placement, the medical operator may refer to the tab 112 to aid in positioning the sling assembly 100. If necessary, the push tubes 202 and 302 and/or dilator tubes 107 and 108 may be rotated one or more times to reduce twisting or other deformation that may have occurred to the sling 102 and/or sling assembly 100.

Figure 4E:
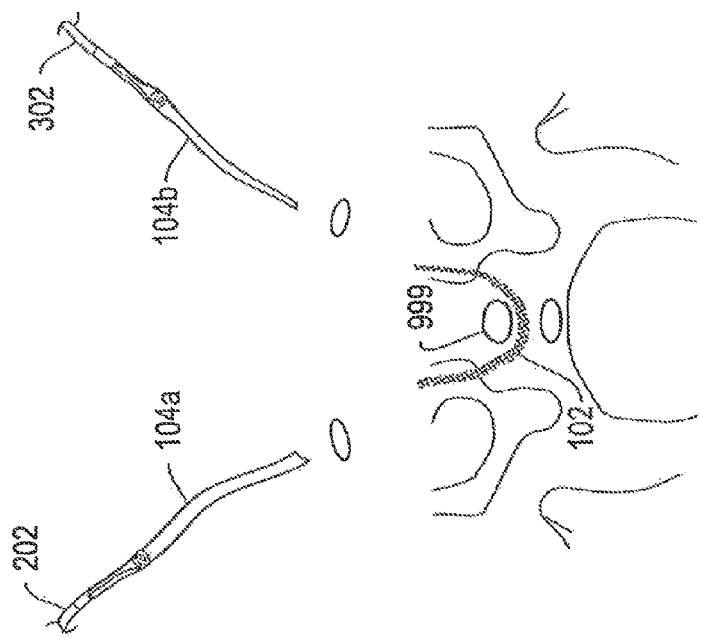
Figure 4F:
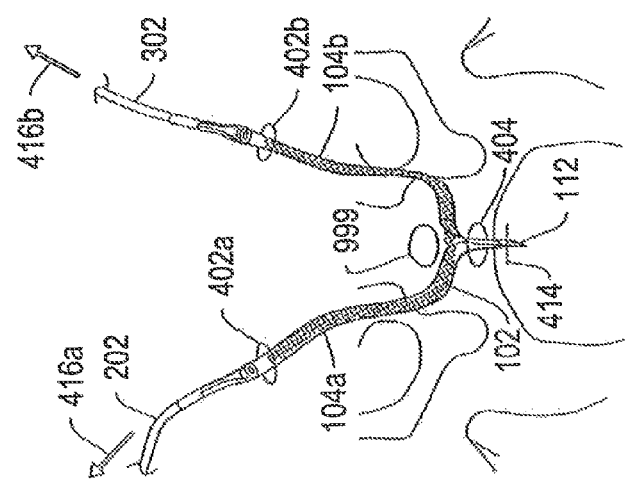

As shown in FIGS. 4E-F, once the sling assembly 100 is suitably placed, the medical operator can cut across the middle of the tab 112, for example, along the dotted line 414, separating sleeve portions 104a and 104b. The tab 112 is discarded, and the operator pulls the push tubes 202 and 302 in the directions of the arrows 416a and 416b, respectively, to slide the sleeve portions 104a and 104b off of the sling 102, and out of the body by way of the abdominal incisions 402a and 402b, leaving the sling 102 positioned in the periurethral tissues below urethra 999. Although in the illustrative embodiment, the push tubes 202 and 302 are shown to be completely out of the body prior to cutting the tab 112, in other embodiments, the sling assembly 100 and the push tubes may be sized such that a portion of the push tube 202 and/or 302 is still within the body at the time the tab 112 is cut.

Figure 5D:
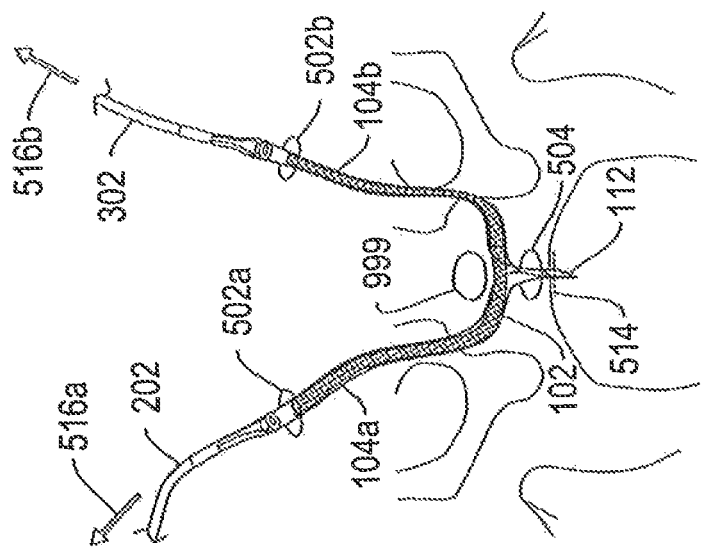

FIGS. 5A-E conceptually depict an illustrative method for transvaginally introducing a sling 102 into the body of a patient using the sling delivery system 200 shown in FIG. 2. As shown in FIG. 5A, incisions 502a and 502b are made on each side of the midline of the body in the lower abdomen along with an incision 504 made in the vaginal wall of the patient. The push tube 202 is inserted into the lumen 106a of the dilator tube 107 of the delivery device 100. According to this illustrative embodiment, the distal tip 212e of the shaft 212 of the delivery device 208 is inserted into the second end 202b of the push tube 202 until at least the shaft tip 212e and at least part of the straight portion 212d extend beyond the first end 202a. With the sling delivery system 500 so assembled, the distal tip 212e of the shaft 212 is inserted into the vaginal wall incision 504 in the direction of the arrow 506 to create a passage up along the posterior surface of the pubic bone through body tissue. The passage is created by moving the shaft 212 in from the vaginal wall incision 504 and out through the abdominal wall incision 502a. As the shaft is inserted into the body by way of the vaginal incision 504, the push tube 202 also passes into the body. If the push tube 202 slides on the shaft 212 during insertion, the shoulder 204 may abut the handle 210. Continued insertion advances the push tube first end 202a out of the body through the abdominal incision 502a.

As shown in FIG. 5B, the first end 202a of the push tube 202 is then grasped by the medical operator and the delivery device 208 is retracted out of the body in the direction of the arrow 508. Although the illustrative embodiment of FIG. 5B depicts the second end 202b of the push tube 202 extending out of the body at the vaginal incision 504 at the same time the first end 202a is extending out the abdominal incision 502a, this need not be the case. In some embodiments, the push tube 202 is sized such that the second end 202b is within the body when the first end 202a protrudes from the abdominal incision 502a.

Figure 5C:
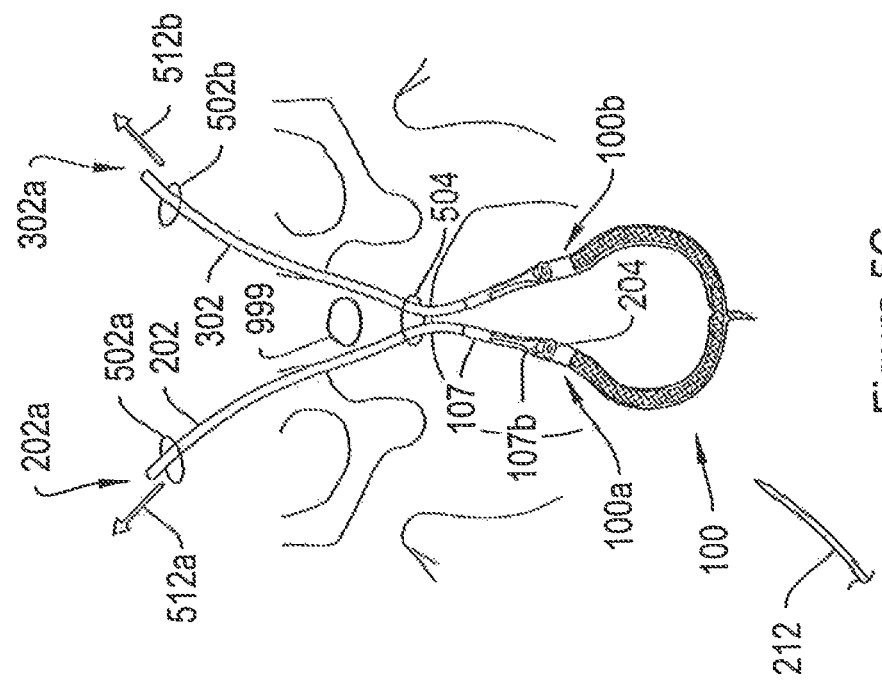

As shown in FIG. 5C, the procedures described above for FIGS. 5A-B are then repeated with the delivery device 208 and the push tube 302 on the contralateral side of the body. With both the push tubes 202 and 302 inserted, a cystoscopy may be performed to verify correct placement and ensure bladder integrity. Subsequent to placement verification, the medical operator grasps the ends 202a and 302a and gently pulls in the direction of the arrows 512a and 512b, respectively. This pulls the push tubes 202 and 302 through the body from the vaginal incision 504 at least partially out the abdominal incisions 502a and 502b, respectively. By pulling alternatively on the ends 202a and 302a, the medical operator places the sling assembly 100 at the desired location under the urethra 999. During placement, the medical operator may refer to the tab 112 to aid in positioning the sling assembly 100. If necessary, the push tubes 202 and 302 and/or dilator tubes 107 and 108 may be rotated one or more times to reduce twisting or other deformation that may have occurred to the sling 102 and/or sling assembly 100.

As shown in FIGS. 5D-E, once the sling assembly 100 is suitably placed, the medical operator can cut across the middle of the tab 112, for example, along the dotted line 514, separating sleeve portions 104a and 104b. The tab 112 is discarded, and the operator pulls the push tubes 202 and 302 in the directions of the arrows 516a and 516b, respectively, to slide the sleeve portions 104a and 104b off of the sling 102, and out of the body by way of the abdominal incisions 502a and 502b, leaving the sling 102 positioned in the periurethral tissues below urethra 999. Although in the illustrative embodiment, the push tubes 202 and 302 are shown to be completely out of the body prior to cutting the tab 112, in other embodiments, the sling assembly 100 and the push tubes may be sized such that a portion of the push tube 202 and/or 302 is still within the body at the time the tab 112 is cut.

Figure 6:
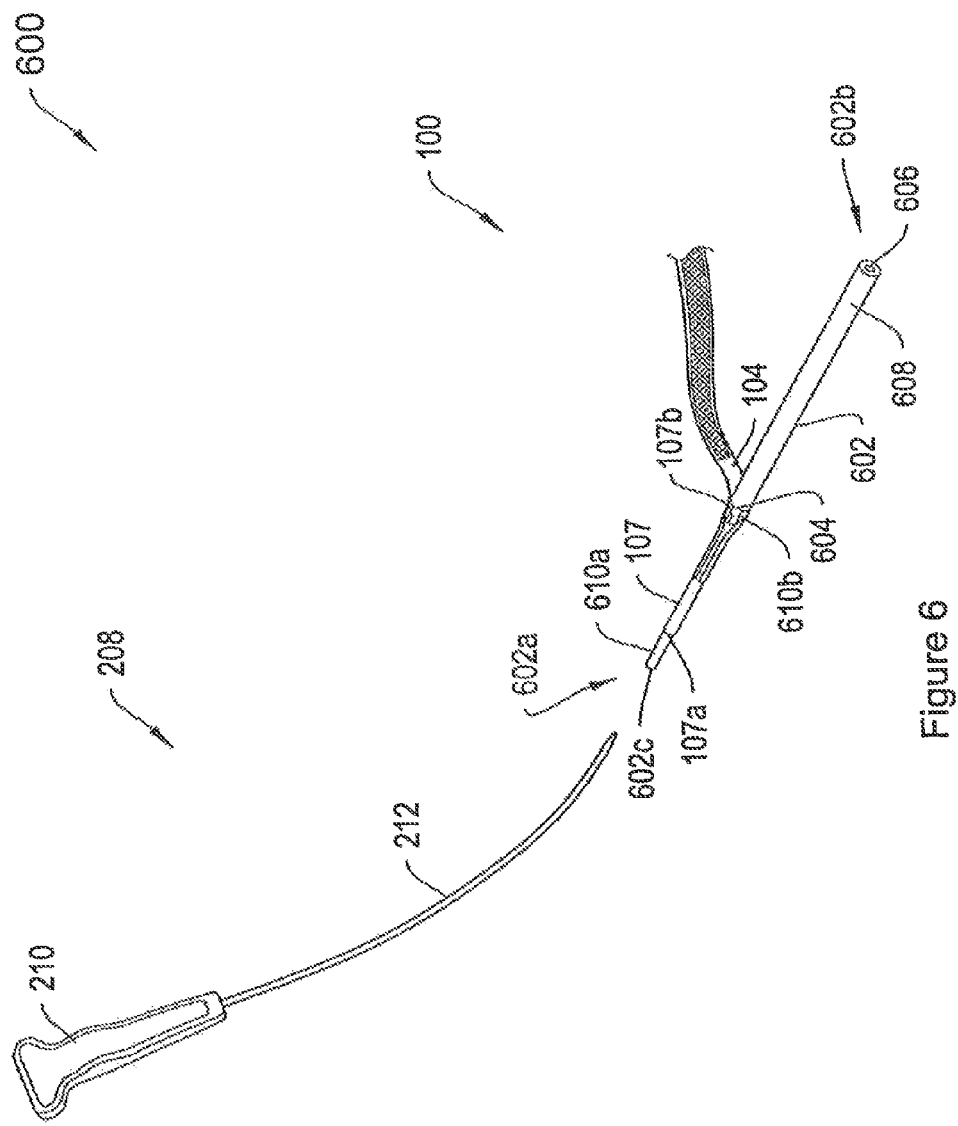
FIG. 6 depicts a sling delivery system employing the sling assembly of FIG. 1 and an alternative push tube according to another illustrative embodiment of the invention.

FIG. 6 shows a perspective view of an assembled sling delivery system 600 according to another illustrative embodiment of the invention. The system 600 includes the delivery device 208, the sling assembly 100, and a push tube 602. The push tube 602 includes a first end 602a, a second end 602b, and a longitudinally extending through lumen 606, which runs the length of the push tube between the first 602a and second 602b ends. The push tube 602 also includes a first portion 608 having a first outside diameter and a second portion 610 having a second outside diameter less than that of the first portion 608. A shoulder 604 is formed at the transition between the first and second outside diameters.

The reduced diameter portion 610 of the push tube 602 is sized and shaped to slidably move through and interfit within the lumen 106a of the dilator tube 107. The portion 610 can advance through the lumen 106a in the direction of the exterior end 107a of the dilator tube 107 until the shoulder 604 abuts the dilator tube interior end 107b. In some instances, a segment 610a of the reduced diameter portion 610 extends beyond the exterior end 107a of the dilator tube 107, and another segment 610b of the reduced diameter portion 610 extends beyond the interior end 107b of the dilator tube 107. The shoulder 604 is sized and shaped to prohibit its passage through the lumen 106a (shown in FIG. 1) of the dilator tube 107, i.e. the shoulder 604 has a greater outside diameter than the inside diameter of the lumen 106a. The illustrative embodiment of FIG. 6 depicts only one shoulder 604. However, the push tube 602 may include more than one shoulder 604, for example, such as described in further detail below with respect to FIG. 10. Also, the push tube portions 608 and 610 may each have uniform diameters that gradually increase or decrease one or more times, to provide bumps, ridges, and/or grooves, for example. In other embodiments, the two portions 608 and 610 have equal outside diameters with the radially extending shoulder 604 having a larger diameter than either portion and separating the two equal diameter portions.

The lumen 606 may have a uniform diameter or may include one or more locations of increased and/or decreased diameter. For example, the inner walls of the push tube 602 defining the lumen 606 may include bumps, ridges, shoulders, grooves, or other internal protuberances for increasing or decreasing the diameter of the lumen 606. As mentioned above for the lumen 206 of the push tube 202, the lumen 606 is sized and shaped so that the shaft 212 of the delivery device 208 slidably interfits within the lumen 606. Depending on the sling implantation method, the shaft 212 may enter the lumen 606 from either the first end 602a or the second end 602b of the push tube 602. The push tube 602 may also include a tip 602c having a taper and/or decreased outside diameter. For example, the tip 602c may be conical in shape.

Figure 7:
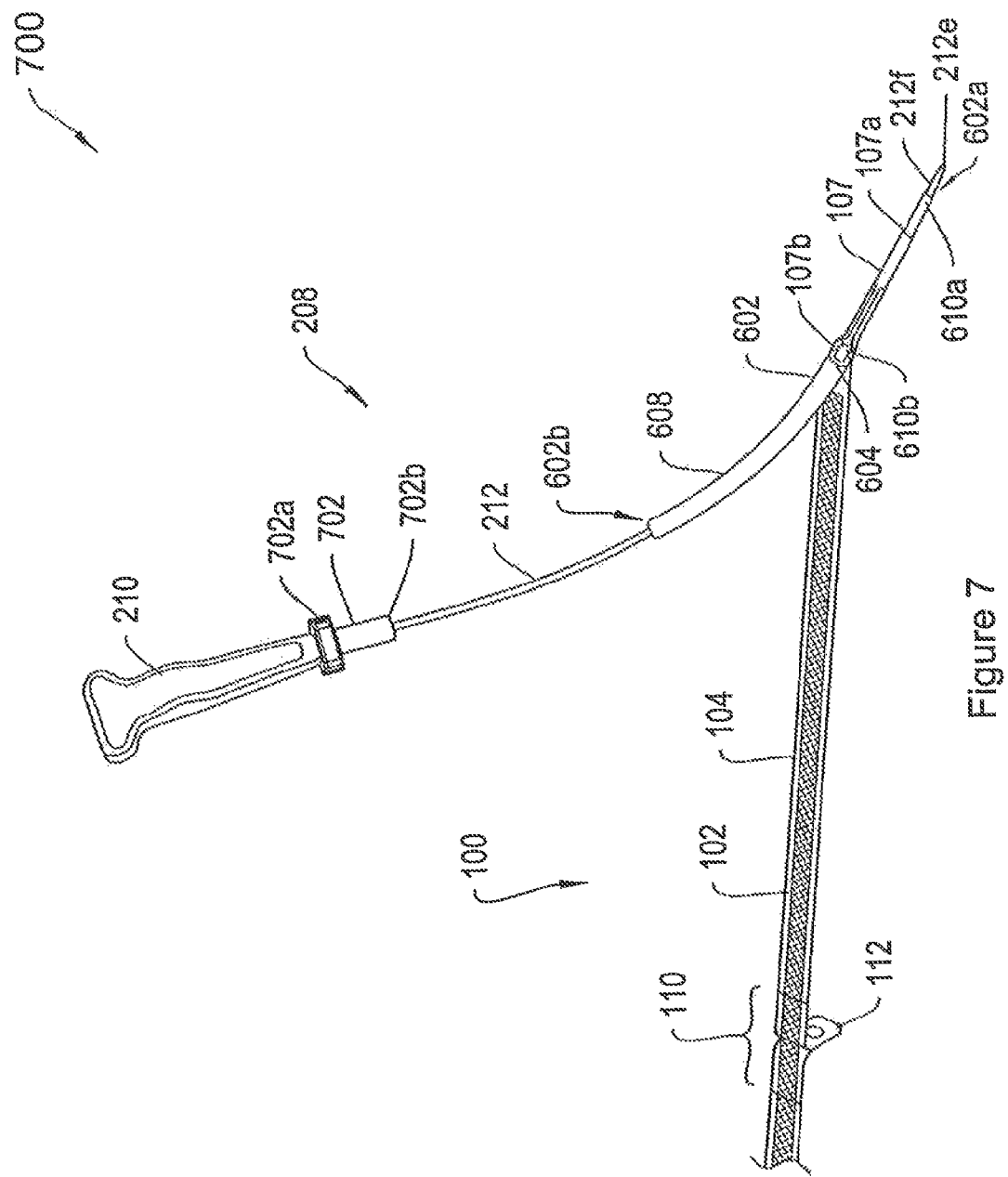
FIG. 7 depicts a sling, delivery system similar to that of FIG. 6 assembled for introducing a sling via a transvaginal implantation method according to another illustrative embodiment of the invention.

FIG. 7 shows a perspective view of an assembled sling delivery system 700 according to another illustrative embodiment of the invention. The system 700 includes the delivery device 208, the sling assembly 100, and the push tube 602. Delivery device 208 is fitted with optional pusher mechanism 702. As shown in the illustrative embodiment of FIG. 7, the push tube 602 slidably interfits with the dilator tube 107 of the sling assembly 100 as described above for FIG. 6. The reduced diameter portion 610 of the push tube 602 slidably interfits within the lumen 106a of dilator tube 107 such that a segment 610a extends beyond the exterior end 107a of the dilator tube. The shaft 212 of delivery device 208 slidably interfits into lumen 606 at the second end 602b of push tube 602. A portion 212f of the shaft 212 extends through the lumen 606 and beyond the first end 602a of the push tube 602.

An optional pusher mechanism 702 slidably interfits onto the shaft 212 of the delivery device 208 such that the pusher mechanism can freely slide over any portion of the shaft 212. In the illustrative embodiment, the pusher mechanism 702 interfits onto shaft the 212 prior to insertion of the shaft into the lumen 606. The pusher mechanism 702 includes a grasping area 702a for grasping by a medical operator and a distal surface 702b. In the illustrative embodiment, the distal surface 702b has a similar or larger external diameter than the portion 608 of the push tube 602 at second end portion 602b so that in the course of advancement of the pusher mechanism 702 from the handle 210 to the distal shaft tip 212e the distal surface 702b abuts the second end 602b of the push tube 602.

In other embodiments, the pusher mechanism 702 tapers in diameter, and a portion closest to the grasping area 702a has a larger diameter than the distal surface 702b or vice versa. In one such tapered embodiment, the pusher mechanism 702 tapers near the distal surface 702b, and the distal surface 702b has a smaller external diameter than the internal diameter of lumen 606. In this embodiment, the distal surface 702b can be wedged into the lumen 606 between the shaft 212 and the push tube wall defining the lumen 606. Such wedging may serve to dilate the lumen 606 and facilitate sliding of the push tube 602 off the shaft 212.

During use of the system 700, with one hand the medical operator can grasp the delivery device 208 by the handle 210 and with the other hand grasp the pusher mechanism 702 by the grasping area 702a. The medical operator can then advance the pusher mechanism 702 away from the handle 210 toward the distal shaft tip 212e. During the advancement, the distal surface 702b of the pusher mechanism 702 eventually abuts the second end 602b of the push tube 602. Continued advancement of the pusher mechanism 702 advances the push tube 602 into the lumen 106a of the dilator tube 107 until shoulder the 604 abuts the interior end 107b of the dilator tube. Further advancement of the pusher mechanism 702 advances the push tube 602, along with the dilator tube 107, off of the shaft 212.

FIGS. 8A-D conceptually depict an illustrative method for transvaginally introducing a sling 102 into the body of a patient using the sling delivery system 700 shown in FIG. 7. As shown in FIG. 8A, incisions 802a and 802b are made on each side of the midline of the body in the lower abdomen along with an incision 804 made in the vaginal wall of the patient. The assembled sling delivery system 700 includes the delivery device 208, the sling assembly 100, and the push tube 602. The shaft 212 of the delivery device 208 is inserted into the vaginal wall incision 804 in the direction of the arrow 806 to create a passage up along the posterior surface of the pubic bone through body tissue. The passage is created by moving the shaft 212 in from the vaginal wall incision 804 and out through the abdominal wall incision 802a. As the shaft 212 is inserted into the body by way of the vaginal incision 804, the push tube 602 also passes into the body. If the push tube 602 slides on shaft 212 during insertion, the second end 602b may abut the distal surface 702b of pusher mechanism 702.

As shown in FIG. 8B, the medical operator grasps the handle 210 of the delivery device 208 and holds the device, while the other hand grasps the grasping area 702a of the pusher mechanism 702. The medical operator then slidably advances the pusher mechanism 702 distally up the shaft 212. When the distal surface 702b abuts the second end 602b of the push tube 602, continued distal advancement of the pusher mechanism pushes the push tube 602 into the body of the patient through vaginal incision 804. Advancement continues in the direction of arrow 809 until the first end 602a of the push tube 602 emerges from the abdominal incision 802a. The medical operator then grasps the first end 602a while the delivery device 208 is retracted in the direction of the arrow 808. The shaft 212 is pulled out from the lumen 606 by way of the second end 602b of the push tube 602. The pusher mechanism 702 remains associated with the shaft 212.

As shown in FIG. 8C, the procedure described above for FIGS. 5A-B is then repeated with the delivery device 208 and the push tube 682 on the contralateral side of the body. With both the push tubes 602 and 682 inserted, a cystoscopy may be performed to verify correct placement and ensure bladder integrity. Subsequent to placement verification, the medical operator grasps the ends 602a and 682a and gently pulls in the direction of the arrows 812a and 812b, respectively. This pulls the push tubes 602 and 682 through the body from the vaginal incision 804 and at least partially out the abdominal incisions 802.a and 802b, respectively. By pulling alternatively on the ends 602a and 682a, the operator places the sling assembly 100 at the desired location under the urethra 999. During placement, the medical operator may refer to the tab 112 to aid in positioning the sling assembly 100. If necessary, the push tubes 602 and 682 and/or dilator tubes 107 and 108 may be rotated one or more times to reduce twisting or other deformation that may have occurred to the sling 102 and/or sling assembly 100.

As shown in FIGS. 8C-D, once the sling assembly 100 is suitably placed, the operator can cut across the middle of the tab 112, for example, along the dotted line 814, separating the sleeve portions 104a and 104b. The tab 112 is discarded, and the operator pulls the push tubes 602 and 682 in the directions of the arrows 812a and 812b, respectively, to slide the sleeve portions 104a and 104b off of the sling 102, and out of the body by way of the abdominal incisions 802a and 802b, leaving the sling 102 positioned in the periurethral tissues below urethra 999. Although in the illustrative embodiment, the reduced diameter portions 610 and 680 of the push tubes 602 and 682, respectively, are shown to be completely out of the body prior to cutting the tab 112, in other embodiments, the sling assembly 100 and the push tubes may be sized such that a segment of the portion 610 and/or 680 is still within the body at the time the tab 112 is cut.

Figure 9:
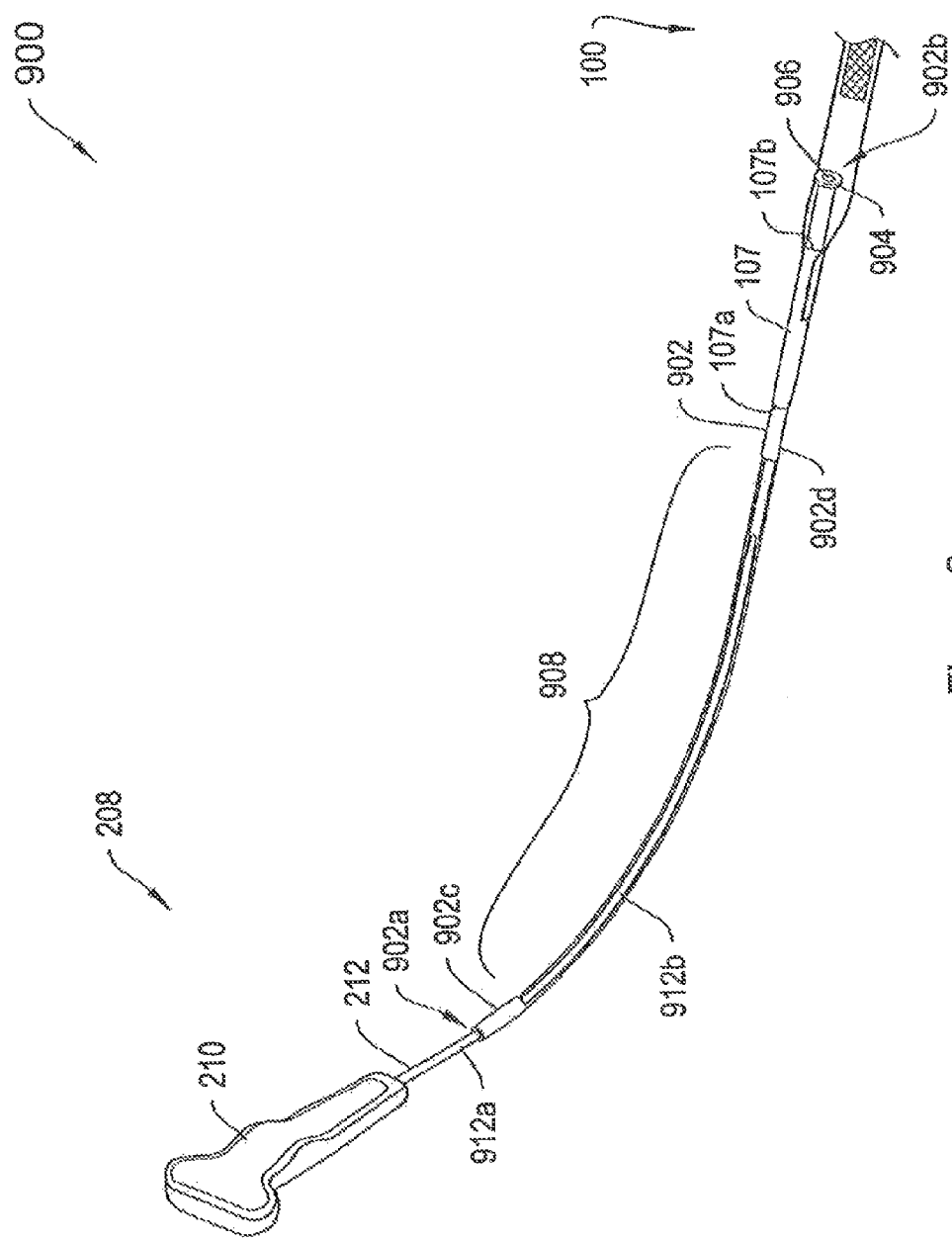
FIG. 9 depicts a sling delivery system employing a push tube with an axially extending cut out according to an illustrative embodiment of the invention.

FIG. 9 shows a perspective view of an assembled sling delivery system 900 according to another illustrative embodiment of the invention. The system 900 includes the sling assembly 100, the delivery device 208, and a push tube 902. The push tube 902 includes a first end 902a and a second end 902b. The push tube 902 also includes a shoulder or flared end 904 located at the second end 902b where the outer diameter of the push tube is substantially greater than that of the remaining portion of the push tube. The push tube 902 also includes a longitudinally extending through lumen 906, which runs the length of the push tube between the first 902a and second 902b ends, and a window section 908 where a portion of the push tube wall is absent.

Similar to push tube 202 of FIGS. 2-3, the push tube 902 is sized and shaped to slidably move through the lumen 106a of the dilator tube 107. In the illustrative embodiment, the push tube 902 is free to advance through the dilator tube 107 in the direction of the exterior end 107a of the dilator tube until the flared shoulder 904 of the push tube 902 abuts the interior end 107b of the dilator tube 107. The outer diameter of the shoulder 904 is greater than the diameter of the lumen 106a of the dilator tube 107, and prevents the push tube 902 from advancing completely through the dilator tube 107 in the direction of the exterior end 107a.

In the illustrative embodiment of FIG. 9, the shaft 212 of delivery device 208 slidably interfits into the first end 902a of the lumen 906 of the push tube 902. In other embodiments, the shaft 212 may be inserted into the second end 902b of the push tube 902. In the illustrative embodiment, a portion of the shaft 912a is not within the lumen 906, while another portion 912b is within the lumen. In some embodiments, the push tube 902 is flexible and can bend and conform to the shape of the dilator tube 107 and/or the shape of the shaft 212 of the delivery device 208. In other embodiments, the push tube 902 is semi-rigid or rigid. Although in the illustrative embodiment of FIG. 9 the shaft 212 is depicted as being curved for a transabdominal or a transvaginal implantation method, the shaft 212 may be shaped in any suitable manner and include substantially straight, angled, and/or helical portions. Other shaft shapes, such as a helical shape, may be suitable for other implantation methods, such as a transobtural method.

The push tube 902 also includes a window section 908, wherein a portion of the push tube wall that defines the lumen 906 is removed, absent, or cut out, thus exposing the lumen 906. The window section 908 is located intermediate to the first 902a and the second 902b ends. Along window section 908, a portion of the wall of the push tube 902 is removed to define two sections 902c and 902d where the wall of the push tube is not removed. As shown in the illustrative embodiment of FIG. 9, the portion 912b of the shaft that is within the window section 908 is exposed. The window section 908 facilitates sliding of the shaft 212 within the lumen 906 of the push tube 902 since there is less surface area for contact between shaft 212 and the inner walls of the push tube.

Figure 10:
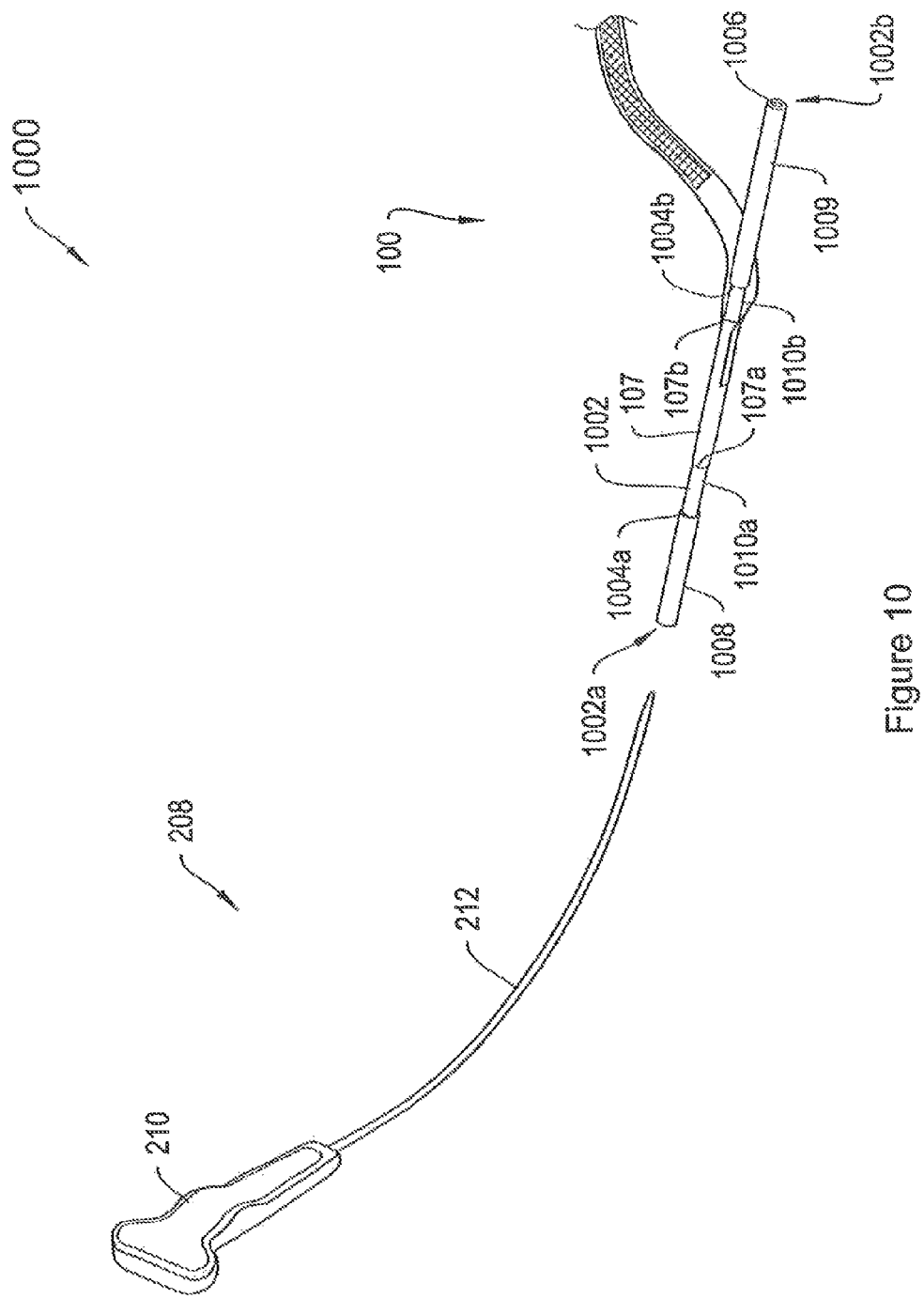
FIG. 10 depicts a sling delivery system employing the sling assembly of FIG. 1 and an alternative push tube according to another illustrative embodiment of the invention.

FIG. 10 shows a perspective view of an assembled sling delivery system 1000 according to another illustrative embodiment of the invention. The system 1000 includes the sling assembly 100, the delivery device 208, and a push tube 1002. The push tube 1002 includes a first end 1002a and a second end 1002b, and a longitudinally extending through lumen 1006, which runs the length of the push tube between the first 1002a and second 1002b ends. The push tube 1002 also includes two end portions 1008 and 1009 located near ends the 1002a and 1002b, respectively. Located intermediate to the ends 1002a and 1002b and between the end portions 1008 and 1009 is an intermediate portion 1010, which is smaller in outer diameter than the end portions 1008 and 1009. A shoulder 1004a is formed by the transition between the end portion 1008 and the intermediate portion 1010. Similarly, a shoulder 1004b is formed by the transition between the end portion 1009 and the intermediate portion 1010.

The intermediate portion 1010 is sized and shaped to slidably move through the lumen 106a of the dilator tube 107. The intermediate portion 1010 can advance through the lumen 106a of the dilator tube 107 in the direction of the exterior end 107a or the interior end 107b until the flared shoulder 1004b or 1004a of the push tube abuts the interior end 107b or the exterior end 107a. The outer diameters of the shoulders 1004a and 1004b are greater than the internal diameter of the lumen 106a, and the shoulders 1004a and 1004b are prevented from advancing within the lumen. As a result, the intermediate portion 1010 cannot slide completely out from the lumen 106a of the dilator tube 107, and the push tube 1002 remains slidably attached to the sling assembly 100.

As shown in the illustrative embodiment of FIG. 10, a section 1010a of the intermediate portion 1010 may lie beyond the exterior end 107a of the dilator tube 107, and a section 1010b may lie beyond the interior end 107b. In other embodiments, the length of the intermediate portion 1010 may be similar to that of dilator tube 107 such that sections 1010a and/or 1010b are very small or even absent with respect to the overall length of the intermediate portion 1010; such an embodiment may leave little or no space for the intermediate portion 1010 to slide within the lumen 106a.

Although in the illustrative embodiment of FIG. 10 the intermediate portion 1010 is located near the mid point of push tube 1002, in other embodiments the intermediate portion 1010 is located near the first end 1002a or the second end 1002b.

In the illustrative embodiment of FIG. 10, the end portions 1008 and 1009 have outer diameters similar to those of shoulders 1004a and 1004b. In other embodiments, the end portions 1008 and 1009 have smaller or larger outer diameters than the shoulders 1004a and 1004b. As shown in the illustrative embodiment, the end portions 1008 and 1009 have greater external diameters than the intermediate portion 1010. However, in other embodiments, the end portions 1008 and 1009 have similar outer diameters or smaller outer diameters than the intermediate portion 1010; in which case, the end portions 1008 and 1009 have smaller outer diameters than the shoulders 1004a and 1004b. Furthermore, in some embodiments, the end portions 1008 and 1009 can have similar or different outer diameters with respect to one another.

In some embodiments, push tube 1002 is assembled by the medical operator prior to implantation of sling 102; for example, following slidable interfitting of the intermediate portion 1010 within lumen 106a, one or more end portions 1008 and/or 1009 is attached to the intermediate portion 1010, securing push tube 1002 to the sling assembly 100. In other embodiments, the push tube 1002 is assembled during the course of manufacture and may be produced in association with sling assembly 100.

Unless stated otherwise herein, the various components of the invention are made of biocompatible and/or materials, which can include, for example, poly-alpha-hydroxy acids (e.g. polylactides, polyglycolides and their copolymers), polyanhydrides, polyorthoesters, segmented block copolymers of polyethylene glycol and polybutylene terephtalate (Polyactive™), tyrosine derivative polymers or poly(ester-amides), polyethylene/ethylene vinyl acetate (EVA) blend, polyethylene, polyester, nylon, polypropylene, thermoplastic fluorinated ethylene propylene (FEP), TFP, stainless steel, malleable metal or any combination of these materials. In certain embodiments, the delivery assemblies of the invention include cadaveric, animal, and/or autologous human tissue.

The drawings disclosed herein are not necessarily to scale; emphasis instead is generally placed upon illustrating the principles of the invention.

Variations, modifications, and other implementations of what is described herein will occur to those of ordinary skill without departing from the spirit and the scope of the invention. Accordingly, the invention is not to be limited only to the preceding illustrative description. For additional illustrative features that may be used with the invention, including the embodiments described here, refer to the documents listed herein above and incorporated by reference in their entirety. All operative combinations between the above described illustrative embodiments and those features described in U.S. patent application Ser. No. 10/642,365, entitled "Systems, Methods and Devices Relating to Delivery of Medical Implants," U.S. patent application Ser. No. 10/642,365, entitled "Systems, Methods and Devices Relating to Delivery of Medical Implants," and U.S. patent application Ser. No. 10/957,926, entitled "Systems and Methods for Delivering a Medical Implant to an Anatomical Location in a Patient," are considered to be potentially patentable embodiments of the invention. The contents of all references, patents and published patent applications cited throughout this Application, as well as their associated figures are hereby incorporated by reference in entirety.

Many equivalents to the specific embodiments of the invention and the specific methods and practices associated with the systems and methods described herein exist. By way of example, in addition to being used for tranabdominal and transvaginal delivery of an implantable sling, the invention may also be employed with a transobtural implantation procedure. In one such procedure, a shaft of a delivery device is introduced through an incision in the ischiopubic region and passed through an obturator foramen and through the vaginal wall. A push tube may then be slid over the end of the shaft extending through the vaginal wall. The push tube may be passed along the shaft through the obturator foramen until an end of the push tube extends through the ischiopubic incision. Alternatively, the shaft may be withdrawn sufficiently to pull the push tube end out the ischiopubic inscision. The medical operator can then grasp the push tube and withdraw the delivery device to leave a portion of the sling assembly within the body of the patient. The procedure may be repeated on the contralateral side of the body with the same or a second delivery device. The medial operator can then use the push tubes to adjust the sling location and then remove any protective sleeve as described above for other procedures.

Removal of the push tubes and sleeve may leave the sling ends positioned near or through the respective obturator membranes.

Accordingly, the invention is not to be limited to the embodiments, methods, and practices disclosed herein.

What is claimed is:

1. A method of treating urinary incontinence comprising implanting a surgical sling in a patient via a vaginal cavity, comprising:
   slidably interfitting a first push tube into a first dilator tube, the first dilator tube being disposed at an end of a sling assembly;
   slidably interfitting the first push tube onto an end of a shaft of a delivery device;
   inserting the shaft transvaginally through a vaginal wall of the patient;
   removing the shaft from the patient to implant a portion of the sling assembly in periurethral tissue of the patient;
   slidably interfitting a second push tube into a second dilator tube, the second dilator tube being disposed at a second end of the sling assembly;
   slidably interfitting the second push tube onto the end of the shaft of the delivery device;
   inserting the shaft transvaginally through the vaginal wall of the patient; and
   removing the shaft from the patient to implant a second portion of the sling assembly in periurethral tissue of the patient.

2. The method of claim 1, further comprising sliding the first push tube along the shaft until it extends through an abdominal incision prior to removing the shaft.

3. The method of claim 2, further comprising grasping the first push tube where it extends through the abdominal incision prior to removing the shaft.

4. The method of claim 1, further comprising sliding the first push tube along the shaft with a pusher mechanism of the delivery device.

5. The method of claim 1, further comprising sliding the second push tube along the shaft until it extends through an abdominal incision prior to removing the shaft.

6. The method of claim 5, further comprising grasping the second push tube where it extends through the abdominal incision prior to removing the shaft.

7. The method of claim 1, further comprising sliding the second push tube along the shaft with a pusher mechanism of the delivery device.

8. A method of treating urinary incontinence comprising:
   interfitting a first push tube onto a shaft of a delivery device, the first push tube being disposed within a first tube included on a sling assembly at a first end of the sling assembly;

inserting the shaft transvaginally through a vaginal wall of a patient;

removing the shaft from the patient to implant a portion of the sling assembly in periurethral tissue of the patient;

slidably interfitting a second push tube onto the shaft of the delivery device, the second push tube being disposed within a second tube included on the sling assembly at a second end of the sling assembly;

inserting the shaft transvaginally through the vaginal wall of the patient; and removing the shaft from the patient to implant a second portion of the sling assembly in periurethral tissue of the patient.

9. The method of claim 8, further comprising, prior to removing the shaft from the patient, sliding the first push tube along the shaft until it extends through an abdominal incision in the patient.

10. The method of claim 8, further comprising sliding the first push tube along the shaft with a pusher mechanism of the delivery device.

11. The method of claim 8, further comprising sliding the second push tube along the shaft until it extends through an abdominal incision prior to removing the shaft.

12. The method of claim 8, further comprising sliding the second push tube along the shaft with a pusher mechanism of the delivery device.

13. The method of claim 8, further comprising:

cutting a sleeve included in the sling assembly;

pulling the first push tube through a first abdominal incision in the patient to remove a first portion of the sleeve from the patient; and pulling the second push tube through a second abdominal incision in the patient to remove a second portion of the sleeve from the patient.

14. The method of claim 13, wherein:

removing the first portion of the sleeve from the patient includes removing the first tube included on the sling assembly from the patient; and removing the second portion of the sleeve from the patient includes removing the second tube included on the sling assembly from the patient.

15. The method of claim 8, further comprising:

cutting a sleeve included in the sling assembly; and pulling the first push tube through an abdominal incision in the patient to remove at least a portion of the sleeve from the patient.

16. The method of claim 15, wherein removing the at least a portion of the sleeve from the patient includes removing the first tube included on the sling assembly from the patient.

17. The method of claim 8, further comprising:

cutting a sleeve included in the sling assembly; and pulling the second push tube through an abdominal incision in the patient to remove at least a portion of the sleeve from the patient.

18. The method of claim 17, wherein removing the at least a portion of the sleeve from the patient includes removing the second tube included on the sling assembly from the patient.

* * * * *